US006751491B2

United States Patent
Lew et al.

(10) Patent No.: US 6,751,491 B2
(45) Date of Patent: Jun. 15, 2004

(54) ANALYTE MEASURING BIOSENSOR CHIP USING IMAGE SCANNING SYSTEM

(76) Inventors: Seok Lew, 6561 Nod Hill Rd. #32, Salt Lake City, UT (US) 84121; In Suk Han, 11591 S. Terendale La., Salt Lake City, UT (US) 84092

(*) Notice: Subject to any disclaimer, the term of this patent is extended or adjusted under 35 U.S.C. 154(b) by 193 days.

(21) Appl. No.: 10/054,660

(22) Filed: Jan. 22, 2002

(65) Prior Publication Data

US 2003/0100822 A1 May 29, 2003

Related U.S. Application Data

(60) Provisional application No. 60/316,731, filed on Sep. 1, 2001.

(51) Int. Cl.$^7$ ............................................... A61B 5/05
(52) U.S. Cl. ................. 600/345; 600/347; 204/403.11; 204/415
(58) Field of Search ................. 600/345–350, 600/411, 427, 437; 204/403.01–403.15, 414, 415

(56) References Cited

U.S. PATENT DOCUMENTS

| | | | |
|---|---|---|---|
| 4,703,756 A | | 11/1987 | Gough et al. |
| 5,854,078 A | * | 12/1998 | Asher et al. ................. 436/133 |
| 6,201,980 B1 | * | 3/2001 | Darrow et al. .............. 600/347 |
| 6,268,161 B1 | | 7/2001 | Han et al. |
| 6,546,268 B1 | * | 4/2003 | Ishikawa et al. ............ 600/345 |
| 6,593,588 B1 | * | 7/2003 | Reimer ........................ 250/573 |

OTHER PUBLICATIONS

Allcock, H.R., Ambrosia, A.M., "Synthesis and characterization of pH–sensitive poly(organophosphazene) hydrogels," Biomaterials, 1996, pf 2295–2302, vol 17.

Batich, C.D., Yan, J., Bucaria, C, Jr., Elsabee, M., "Swelling Behavior of pH–Sensitive Copolymers Based on Styrene and 4–(or 2–)Vinylpyridine," Macromolecules, 1993, p. 4675–4680, vol 26.

Brannon–Peppas, K., Peppas, N.A., "Dynamic and equilibrium swelling behavior of pH–sensitive hydrogels containing 2–hydroxyethyl methacrylate," Biomaterials, 1990, p. 635–644, vol. 11.

Bronsted, H., Kopecek, J., Polyelectrolyte Gels: Properties, Preparation, and Application, 1992, p. 285–304, Harland R.S., and P.K., Homme (eds.).

De Moor, C.P., Doh, L., Siegel, R.A., "Long–term structural changes in pH–sensitive hydrogels," Biomaterials, 1991, pf 836–840, vol. 12.

Ghandehari, H., Kopeckova, P., Yeh, P–Y., Kopecek, J., "Biodegradable and pH sensitive hydrogels: synthesis by a polymer–polymer reaction," Macromol. Chem. Phys., 1996, p. 965–980, vol 197.

(List continued on next page.)

Primary Examiner—Robert L. Nasser
(74) Attorney, Agent, or Firm—Mallinckrodt & Mallinckrodt; Robert R. Mallinckrodt

(57) ABSTRACT

An implantable chip biosensor for detecting an analyte in vivo in body fluids comprises an analyte-sensitive hydrogel slab chemically configured to vary its displacement volume according to changes in concentration of an analyte, such as glucose, in a patient's body fluid, the slab being disposed in a groove in a support block. The biosensor chip is 'read' by an external scanner configured to quantifiably detect changes in the displacement volume of the hydrogel slab. The support block is made of rigid or semi-rigid support material to restrain expansion of the hydrogel in all but one dimension, and the groove has one or more openings covered with a semipermeable membrane to allow contact between the patient's body fluid and the hydrogel. The scanning means may be any type of imaging devices such as an ultrasound scanner, a magnetic resonance imager (MRI), or a computerized tomographic scanner (CT) capable of resolving changes in the slab's dimensions.

68 Claims, 16 Drawing Sheets

OTHER PUBLICATIONS

Hisamitsu, I., Kazunori, K., Okano, T., and Sakurai, Y., "Glucose–Responsive Gel from Phenylnorate Polymer and Poly (Vinyl Alchohol): Prompt Response at Physiological pH Through the Interaction of Borate with Amino Group in the Gel," 1997, p. 289–293, Plenum Publishing Co.

Jung, D.-Y., Magda, J.J., Han, I.S., "Catalase effects on glucose–sensitive hydrogels," Macromolecules, 2000, p. 3332–3336, vol 33.

Kataoka, K., Miyazaki, H., Bunya, M., Okano, T., and Sakurai, Y., "Totally Synthetic Polymer Gels Responding to External Glucose Concentration: Their Preparation and Application to On–Off Regulation of Insulin Release," J. Am. Chem. Soc., 1998, p. 12694–12695, vol. 120.

Kataoka, K., Miyazaki, H., Hisamitsu, I., Tanaka, K., Okano, T., and Sakurai, Y., "Novel Glucose–Sensitive Polymers and Hydrogels Based on Phenylborate–Containing Polymers," p. 393–394, Tokyo, Japan.

Kataoka, K., and Miyazaki., H., "Sensitive Glucose–Induced Change of the Lower Critical Solution Temperatyue of Poly (N,N–dimethylacrylatemide–co–3–(acrylamido) phenyl–boronic acid) in Physiological Saline," Macromol., 1994, p. 1061–1062, vol. 27.

Khare, A.R., Peppas, N.A., "Release behavior of bioactive agents from pH–sensitive hydrogels," Biomaterials, 1995, p. 559–567, vol. 21.

Kitano, S ., Hisamitsu, I., Koyama, Y., and Kataoka, K., "Effect of the Incorporation of Amino Groups in a Glucose–responsive Polymer Complex Having Phenylboronic Acid Moieties," Polymers for Advance Technologies, 1991, p. 261–264, vol. 2.

Kitano, S., "Glucose–responsive complex formation between poly(vinyl alcohol) and poly(N–vinyl–2–pyrrolidone) with pendent phenylboronic acid moieties," Makrol. Chem., Rapid Commun., 1991, pf 227–233, vol. 12.

Liu, F., Song., S.C., Mix, D., Baudys, M., and Kim, S.W., "Glucose–Induced Release of Glycosylpoly(ethylene glycol) Insulin Bound to a Soluble Conjugate of Concanavalin A," Bioconjugate Chem., 1997, p. 664–672, vol. 8.

Miyata, T., Asami, N., and Uragami, T., "A reversibly antigen–responsive hydrogel," Nature, 1999, p. 766–769, vol. 399.

Miyata, S., Jikihara, A., Nakamae, K., "Preparation of poly(2–glucosyloxyethyl methacrylate)–concanavalin A complex hydrogel and its glucose–sensitivity," Macrolmol. Chem. Phys., 1996, p. 1135–1146, vol. 197.

Miyazaki, H., Kikuchi, A., Yoshiyuki, K., Okano, T., Sakurai, Y., and Kataoka, K., "Boronate–Containing Polymers as Novel Mitogen for Lymphocytes," Biochemical and Biophysical Research Communications, 1993, p. 829–836, vol. 195, No. 2.

Nakamae., K., Miyata, T., Jikihara, A., and Hoffman, A.S., "Formation of poly(glucosylosyethyl methacrylate)–Concanavalin A complex and its glucose–sensitivity," J. Biomater. Sci Polymer Edn, 1994, p. 79–90, vol. 6, No. 1.

Narang, U., Prasad, P.N., Bright, F.V., "Glucose Biosensor Based on a Sol–Gel–Derived Platform," Anal. Chem., 1994, p. 3159–3144, vol. 66.

Pai, CH., Bae, Y.H., Mack, E.J., Wilson, D.E., and Kim, S.W., "Concanavalin A Microspheres for a Self–Regulating Insulin Delivery System," Journal of Pharmaceutical Sciences, 1992, p. 532–536, vol. 81, No. 6.

Pai, C.H., Jacobs, H., Bae., Y.H., and Kim, S.W., "Sythesis and Characterization of Solyble Concanavalin A Oligomer," Biotechnology and Bioengineering, 1993, p. 957–963, vol. 41.

Obaidat, A.A., and Park, K., "Characterization of protein release through glucose–sensitive hydrogel membranes," Biomaterials, 1997, p. 801–806, vol. 18.

Obaidat, A.A., and Park, K., "Characterization of Glucose Dependent Gel–Sol Phase Transition of the Polymeric Glucose–Concanavalin A Hydrogel System," Pharmaceutical Research, 1996, p. 989–995, vol. 13., No. 7.

Sato, S., Jeong, S.Y., McRea, J.C., and Kim, S.W., "Self–Regulating Insulin Delivery Systems," Journal of Controlled Release, 1984, p. 67–77, vol. 1.

Shino, D., Murata, Y., Kataoka, K., Koyama, Y., Yokomaya, M., Okano, T., and Sakurai, Y., "Preparation and characterization of a glucose–responsive insulin–releasing polymer device," Biomaterials, 1994, p. 121–128, vol. 15., No. 2.

Shino, D., Kubo, A., Murata, Y., Koyama, Y., Kataoka, K., Kikuchi, A., Sakurai, Y., and Okano, T., "Amine effect on phenylboronic acid complex with glucose under physiological pH in aqueous solution," Biomater. Sci. Polymer Edn., 1996, p. 697–705, vol. 7, No. 8.

Siegel, R.A., Firestone, B.A., "pH–Dependent equilibrium swelling properties of hydrophobic polyelectrolyte copolymer gels," Macromolecules, 1988, p. 3254–3259, vol. 21.

Siegel, R.A., Johannes, I., Hunt, CA.A., Firestone, B.A., "Buffer Effects on Swelling Kinetics in Polybasic Gels," Pharm. Res., 1992, p. 76–81, vol. 9.

Torchillin, V.P., "Polymers as Carriers of Imaging Agents," Biomaterials and Drug Delivery Toward a New Millenium, 2000, p. 593–612, Hanrimwon, Korea.

Vakkalanka, S.K., Brazel, C.S., Peppas, N.A., "Temperature and pH–sensitive terpolymers for modulated deliver of streptokinase," J. Biomater. Sci. Polym., 1996, p. 119–129, ed. 8.

Vasquez, B., Gurruchaga, M., San Roman J. Biomaterials, 1997, p. 521–526, vol. 18.

* cited by examiner

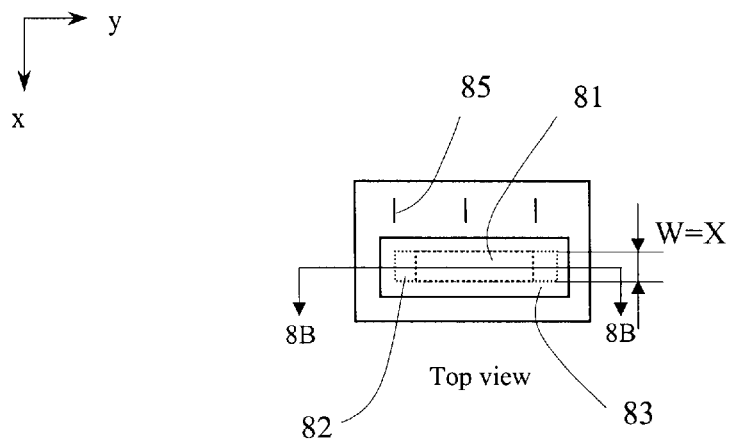
FIGURE 8A
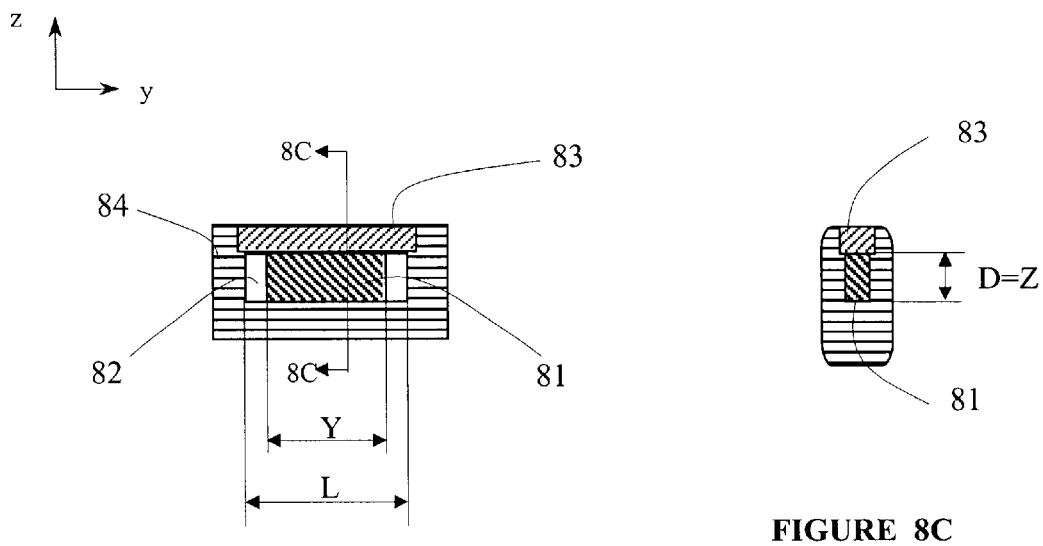
FIGURE 8B
FIGURE 8C

ANALYTE MEASURING BIOSENSOR CHIP USING IMAGE SCANNING SYSTEM

RELATED APPLICATIONS

The present application claims the benefit of Provisional Patent Application Serial No. 60/316,731, filed Sep. 1, 2001, and entitled "Substance sensing system using a hydrogel chip and displacement measuring system".

BACKGROUND OF THE INVENTION

1. Field of Invention

This invention relates generally to biosensors for measuring physiological analytes in humans, and particularly to biosensors suitable for implantation to provide in vivo monitoring of a selected analyte, such as monitoring of blood glucose levels in diabetics.

2. Description of Related Art

For some time the medical community has recognized a need for implantable biosensors to monitor physiologically important analytes. The need is particularly pressing for continuous monitoring of blood glucose in diabetics, since failure to properly maintain glucose levels leads to serious consequences in both the short and long term. The long-term consequences include kidney failure, blindness, and amputation. To date, however, the only test readily available is a fingerstick kit, which does not provide continuous monitoring. Most diabetics use such kits infrequently at best, because of the pain and inconvenience associated with them.

In developing various implantable devices, hydrogels have been widely used as protective biocompatible coatings for the devices. Hydrogels are generally defined as polymeric materials that swell in water and other fluids, absorbing the fluid within the polymer network without dissolving. Hydrophilic hydrogels have a large amount of water content at equilibrium, and good biocompatibility.

Brock et al. describe attempts to make artificial muscle from bundles of extremely thin (10 micron diameter) polyacrylonitrile fibers ("Dynamic Model of Linear Actuator based on Polymer Hydrogel", published on the Web at www.ai.mit.edu/projects/muscle/papers/icim94). The fiber bundles are attached to an artificial tendon with epoxy and thence to a mechanical linkage; the swelling and contraction of the fibers is manipulated by alternately irrigating with acidic and basic solutions. Hydrogels also can be used to mimic human tissue.

The above-described properties of hydrogels make them attractive for use in implantable biosensors. One such device is an implantable amperometric sensor intended to measure glucose levels in blood or body fluids (U.S. Pat. No. 4,703,756 to Gough et al.). A second type of hydrogel biosensor which uses a pressure transducer to measure changes in osmotic pressure in pH-sensitive hydrogels, developed by the present inventors, is described in U.S. Pat. No. 6,268,161 to Han et al., and in co-pending U.S. patent application Ser. Nos. 09/308,392 and 09/644,323.

The Gough et al. biosensor uses the enzymatic activity of glucose oxidase (GOX) to measure glucose levels. GOX catalyzes the conversion of glucose to gluconic acid and hydrogen peroxide ($H_2O_2$), consuming oxygen in the process. The GOX reaction can be followed using electrochemical transducers of various kinds, but the most advanced type of device is the amperometric sensor. In the amperometric method, an electrode produces a current proportional to the diffusional flux of hydrogen peroxide to the electrode surface, or, alternatively, proportional to the diffusional flux of oxygen ($O_2$) to the electrode surface. An increase in the surrounding glucose concentration should increase the diffusional flux of glucose into the membrane and increase the reaction rate within the membrane. The increase in enzymatic reaction rate in turn should increase the local hydrogen peroxide concentration and decrease the local oxygen concentration within the membrane. This increases the current detected by a hydrogen peroxide-based electrode sensor, or decreases the current to an oxygen-based electrode sensor. The latter approach, based on detecting the oxygen flux, requires a reference oxygen-based electrode sensor located in a hydrogel without the enzyme.

A second class of osmotic-pressure hydrogel sensors uses a pressure transducer to directly measure osmotic pressure changes in a hydrogel disposed within a rigid chamber having one open side which is covered with a flexible, semi-permeable diaphragm (Han et al., U.S. Pat. No. 6,268,161; Han et al., U.S. application Ser. Nos. 09/839,993 and 09/644,323). The pressure transducer senses changes in the pressure exerted by the hydrogel on the flexible diaphragm. Two types of such sensors have been developed. One uses pH-sensitive hydrogels having immobilized GOX. In this device, the gluconic acid produced by enzymatic action of GOX on free glucose changes the pH in the fluid matrix, causing it to swell (if the hydrogel has pendant acidic groups) or to shrink (if the hydrogel has pendant basic groups). The second type, which has potentially far wider application, uses the principles of the competitive binding assay. Both analyte and analyte-binding molecules are immobilized within the hydrogel; noncovalent bonds between the two effectively produce crosslinks. When free analyte displaces immobilized analyte, the crosslinking index changes, producing either swelling or shrinking of the hydrogel (depending on other factors in hydrogel composition). The resulting changes in osmotic pressure are measured with a pressure transducer in the same way as for the GOX osmotic-pressure biosensor. Where the analyte is glucose, the immobilized analyte binding molecule may for example be concanavalin A.

A disadvantage of the first two implantable hydrogel-based biosensors described above is the need for a battery for operation of the sensor's transducers and/or for telemetry of sensor readings. Since these are ideally implanted in the patient's body for continuous monitoring of the analyte, repeated invasive procedures are required whenever the battery must be replaced.

Further, so far as we are aware, there is no hydrogel biosensor system in which swelling of an implanted hydrogel is monitored by image capture from outside the body. While ATS Laboratories, Inc. (404 Knowlton St., Bridgeport, Conn. 06608; or on the Web at atslabs.com) manufactures hydrogel phantoms for use in quality control testing of ultrasound machines, these phantoms are strictly external devices, not implanted. Thus, there remains a need for an implantable analyte-sensitive biosensor chip which can be monitored by external imaging.

SUMMARY OF THE INVENTION

A biosensor chip system comprises an analyte-sensitive hydrogel slab chemically configured to vary its displacement volume according to changes in concentration of an analyte in a patient's body fluid, in combination with external scanning means disposed and configured to quantifiably detect changes in the displacement volume of the hydrogel slab. The slab is preferably disposed within an enclosure, channel, or groove on a support block made of rigid or semi-rigid support material; the groove has one or more openings covered with a semipermeable membrane to allow contact between the patient's body fluid and the hydrogel. In a preferred embodiment, the groove is configured to permit expansion of the hydrogel in substantially only one dimension. In a highly preferred embodiment, the hydrogel slab has an elongated filament-like shape, with the length at least about 5 to 50 times the crosswise dimension(s). The scanning means may be any type of imaging device capable of resolving changes in the slab's dimensions when it is implanted within a patient. In a highly presently preferred embodiment, the scanning means is a handheld ultrasound unit; however, other image scanning means including magnetic resonance imagers (MRI) and computerized tomographic scanners (CT) could be used.

Desirably, the biosensor chip also includes a second groove with a reference hydrogel slab, and/or scale marks which can be imaged together with the hydrogel slab to provide a precise dimensional calibration.

The analyte-sensitive slab may be made of any material that alters its displacement volume in response to a change in analyte concentration. Two types of specially chemically configured hydrogels are presently preferred for use in the invention. In one, an oxidative enzyme is immobilized within a pH-sensitive hydrogel, and catalyzes a reaction of the analyte to produce a charged product. The term 'pH-sensitive hydrogel' refers generally to a hydrogel modified to contain pendant charged groups in proportions that produce an overall acidic or basic environment in the fluid within the gel. The immobilized enzyme might be, for example, glucose oxidase, GOX, where the analyte to be measured is glucose. The charged product generated by activity of the enzyme on the analyte causes the hydrogel to change its displacement volume (swell or shrink), which changes can be detected by the scanning means. The second type of hydrogel has both analyte binding molecules (ABMs) and analyte or analyte analogue molecules (AAMs) co-immobilized within it, in addition to charged pendant groups. In the absence of free analyte, immobilized ABMs bind to immobilized AAMs, forming what are in effect non-covalent 'crosslinks'. As free analyte from a body fluid or test solution diffuses into the hydrogel, binding competition displaces immobilized AAMs from ABMs, thus reducing the number of 'crosslinks'. This reduction in crosslinking causes swelling of the hydrogel.

Also, in addition to the above two types of hydrogels, it is within contemplation that other analyte-sensitive swellable materials, polymers, and hydrogels meeting that description may be developed and will be useful in the biosensor. Certain embodiments of the invention are specifically designed to detect glucose levels in body fluids.

In its broadest conception, the invention is an implantable biosensor chip containing an analyte-sensitive hydrogel, which can be imaged by a non-invasive external scanning means such as ultrasound. Such a biosensor chip comprises a support block formed of rigid or semi-rigid, biocompatible material; an enclosure, channel, or groove in the support block having one or more openings permitting penetration of a patient's body fluid; and an analyte-sensitive hydrogel slab disposed within the groove, the hydrogel being chemically configured to vary its displacement volume according to changes in concentration of an analyte in the body fluid.

The invention further encompasses methods of determining the concentration of free analyte in a solution and of making the biosensor chip. The method of determining analyte concentration comprises steps of: providing a hydrogel having pendant charged and/or uncharged moieties, analyte molecules, and analyte-specific binding molecules covalently immobilized therein; contacting the hydrogel sequentially with a series of calibration solutions having known concentrations of free analyte, and measuring the displacement change in the hydrogel for each of the calibration solutions to produce a calibration curve of displacement change versus analyte concentration; contacting the hydrogel with the test fluid, and measuring a resulting displacement change; and comparing the resulting displacement change with the calibration curve to determine the analyte concentration of the test fluid. A further embodiment of the method includes a step of enclosing the hydrogel in a rigid or semi-rigid structure which has at least one permeable portion through which free analyte in the test solution can diffuse into the hydrogel, the structure sized and configured to permit hydrogel expansion in substantially only one dimension.

BRIEF DESCRIPTION OF THE DRAWINGS

The above and other objects, features and advantages of the invention will become apparent after a consideration of the following detailed description presented in connection with the accompanying drawings in which:

FIG. 8A is a top view of an embodiment of a biosensor chip;

FIG. 8B is a vertical section taken on the line 8B—8B in FIG. 8A;

FIG. 8C is a vertical section taken on the line 8C—8C in FIG. 8B;

DETAILED DESCRIPTION

Figure 1:
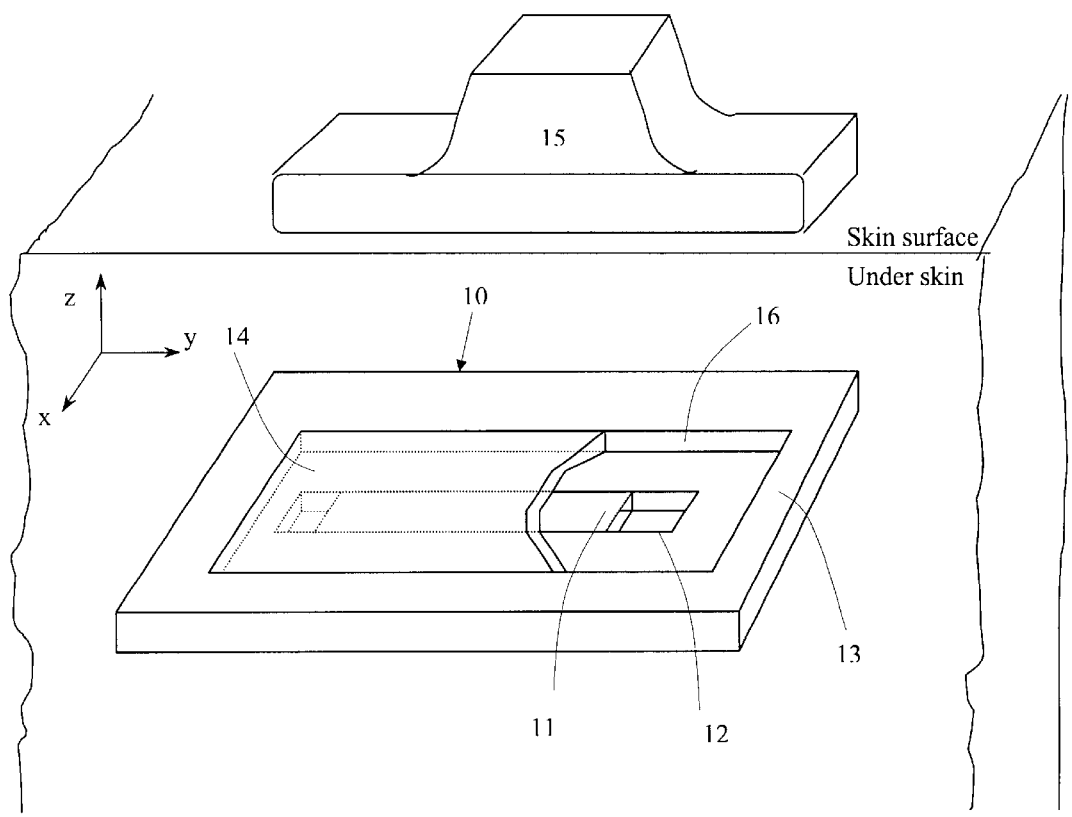
FIG. 1 is a perspective view of one embodiment of an implanted biosensor chip with external scanner with the membrane covering the hydrogel partially broken away.

Referring to FIG. 1, a presently preferred embodiment of a biosensor system has a biosensor chip 10 comprising an elongated slab or filament 11 of analyte-sensitive hydrogel confined in a groove or channel 12 formed in a support block 13 of inert material and overlaid with a semi-permeable membrane 14. The filament 11 of hydrogel is immersed in a biocompatible buffer, such as sterile PBS, which initially fills channel 12. The channel 12 is sized to permit the filament 11 to elongate in the y-direction, but to prevent expansion in the x-direction. The chip 10 is implanted about 5 mm below the skin surface, and an ultrasound scanning device 15 is positioned on the skin surface adjacent to chip 10, when it is desired to read the biosensor chip.

Semi-permeable membrane 14 is secured in receiving recess 16, such as by gluing or heat sealing, and covers the groove 12. Analyte-containing body fluid is free to pass through the membrane 14 and permeate the hydrogel. The membrane 14 will have a thickness on the order of microns. Desirably, membrane 14 and support block 13 will be fully distinguishable from the hydrogel filament 11 and will not interfere with its imaging by the scanning means 15. For the case of ultrasound scanning means, the membrane 14 and support block 13 will thus have a significantly lower density than the hydrogel filament, and will be transparent to the incoming ultrasound wave without absorbing the sound energy so that the hydrogel beneath the membrane can be imaged without interference. In addition, the membrane 14 and support block 13 will be biocompatible and have sufficient stiffness to substantially prevent the hydrogel filament from swelling in directions perpendicular to the longitudinal axis of groove 12.

Block 13 may be formed of any suitable inert, rigid or semi-rigid, biocompatible material, including plastic, Teflon, stainless steel, ceramic, or composites. The outer shape of chip 10 is shown in FIG. 1 to be rectangular, but it may also be cylindrical, cubical, or any other shape that allows easy implantation and affords comfort to users. The material property for block 13 is preferably selected such that the captured hydrogel image can be distinguished from the block image by having significantly different acoustic impedance. Further, while it is presently believed that the best sensitivity will be achieved by confining expansion of the hydrogel to one direction by the use of a rigid or semi-rigid support block 13 forming the groove or channel 12, it may be possible to achieve the goals of the device without rigidly enclosing the gel slab 11. In such case, block 13 (or analogous structure) functions primarily as a support for the gel slab (preventing distortion and deformation of the slab) and as a contrast background to improve scanning resolution. For ultrasound scanning, the material of block 13 should have a density or acoustic impedance sufficiently different from the hydrogel to permit good resolution of the hydrogel slab as an ultrasound image. In the embodiment of FIG. 1, the scanning means is shown to be an ultrasound scanner 15.

The scanning means of the embodiment of FIG. 1 is an ultrasound imaging device. However, other types of imaging systems or scanners may be used, as described subsequently herein. Hydrogels are currently used by ultrasound manufacturers as tissue-mimicking material for determining resolution and in quality control of ultrasound devices, but they are not implanted for such uses. ATS Laboratory of Bridgeport, Conn. is one supplier of tissue-mimicking material and phantoms. However, other types of imaging systems or scanners may be used, as described subsequently herein.

Figure 2:
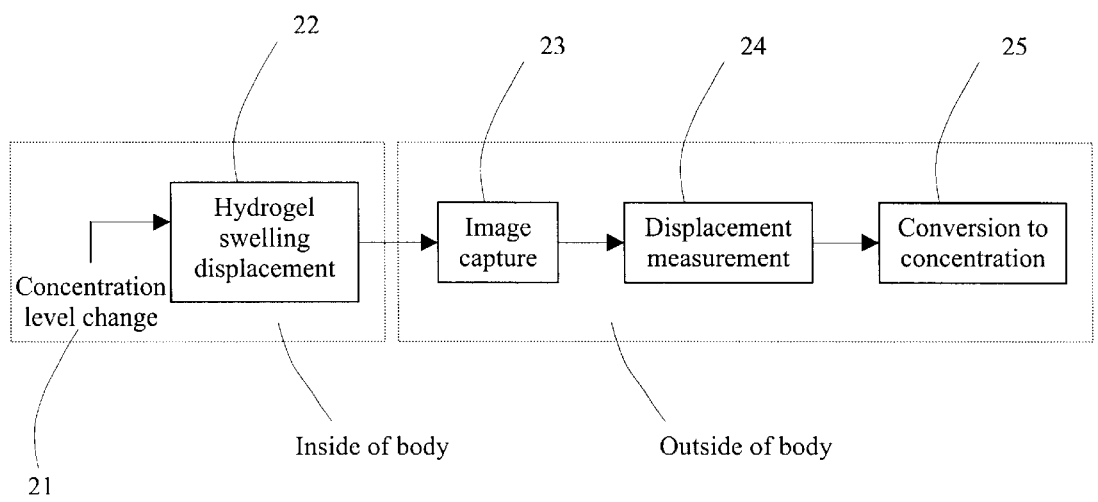
FIG. 2 is a schematic depiction of the measurement of analyte by the biosensor chip system of the invention.

FIG. 2 depicts the general workings of the biosensor chip system for in vivo monitoring of a selected analyte. Changes in analyte concentration 21 in the body fluid produce a change in hydrogel swelling displacement 22; these two aspects of the process occur inside the patient's body. The hydrogel image is captured 23 by scanning means outside body and the displacement change 24 is determined. Finally, the displacement change is converted 25 to the analyte concentration, based on a calibration curve.

Glucose-Sensitive Hydrogel Filament (GSF)

Hydrogels are defined as polymeric materials that swell in water and other solvents, absorbing the fluid within the polymer network without dissolving. Hydrophilic hydrogels have a large amount of water content at equilibrium and good biocompatibility. Hydrogels can be made sensitive to particular analytes, such as glucose. The invention will be further described in relation to glucose sensitive hydrogels wherein the biosensor chip takes the form of a glucose sensor. However, the principles and operation of the biosensor chip will be the same for hydrogels sensitive to other analytes.

There are several ways to make a hydrogel sensitive to glucose. A glucose-sensitive hydrogel will be referred to as GSF. The first type of GSF contains immobilized GOX within pH-sensitive hydrogels, which are copolymers synthesized from various types of methacrylate-derived monomers by free radical solution polymerization. These copolymers are tough, flexible polymers rather than soft hydrogels and are highly biocompatible and inert yet nondegradable in vivo.

A pH-sensitive co-polymeric hydrogel that contains immobilized GOX acts as a sensor of glucose via the conversion of glucose to gluconic acid by the enzyme. The rate of gluconic acid formation is proportional to the glucose concentration in the hydrogel at the reaction location. The changes in glucose concentration in the fluid surrounding the hydrogel result in the changes in the pH value within the hydrogel due to the GOX-catalyzed production of gluconic acid. The gluconic acid protonates pH-sensitive pendant groups in the hydrogel and causes the hydrogel to swell or de-swell, depending on the nature of the pendant groups. If the hydrogel contains basic pendant groups such as diethylaminoethyl methacrylate (DEAMA), it will swell when pH decreases. If it contains acidic pendant groups such as acrylic acid (AA), the hydrogel will shrink when pH decreases. If the GSF is allowed to expand or contract within only one dimension, as is the case for the filament in a rigid or semi-rigid support block, then filament length depends directly on glucose concentration near the hydrogel.

Figure 3:
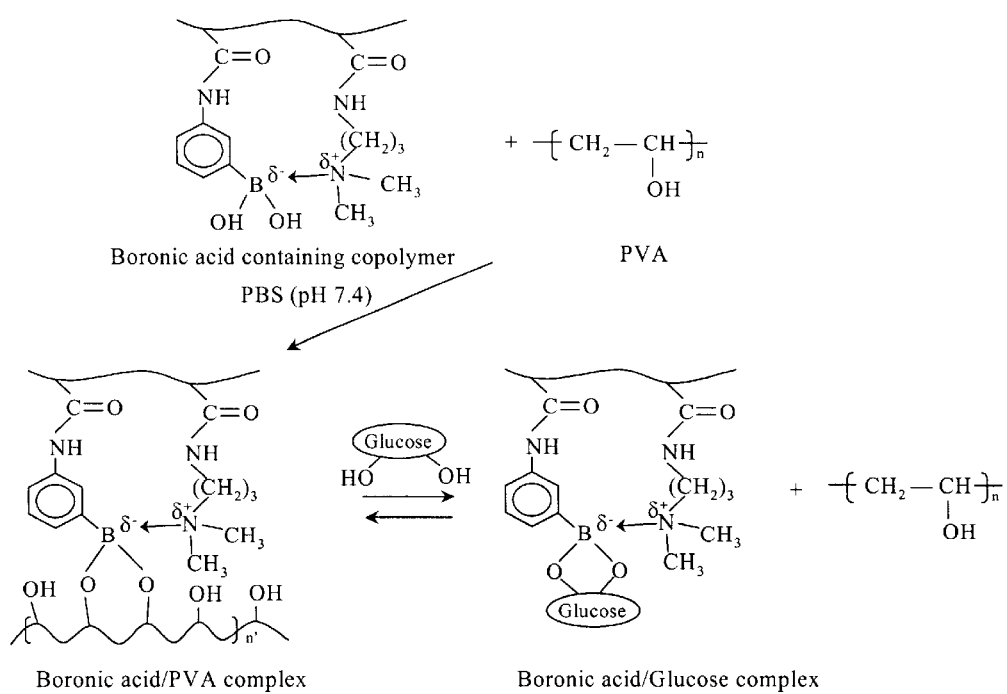
FIG. 3 depicts a competitive binding-type hydrogel based on phenylboronic acid.
Figure 4:
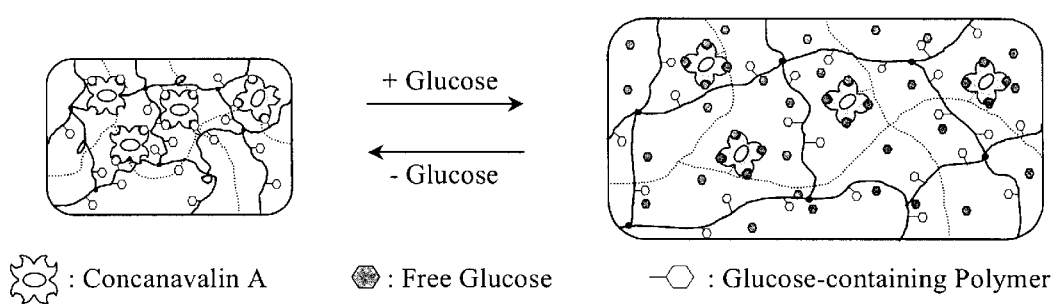
FIG. 4 depicts a competitive binding-type hydrogel based on Concanavalin A, and its swelling mechanism.
Figure 5:
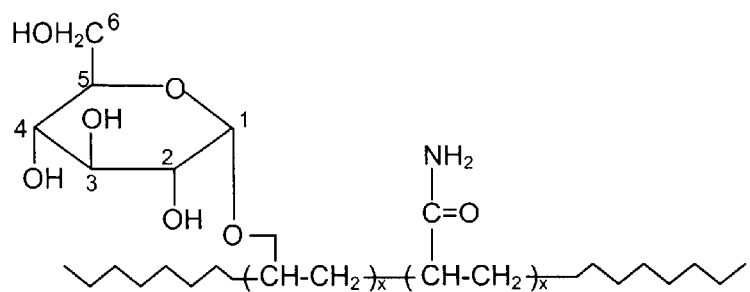
FIG. 5 is an example of vinyl group conjugated glucose.

The second type of GSF is based on a competitive mechanism and does not require oxygen-consuming enzymatic reactions (FIGS. 3, 4). This GSF preferably contains immobilized phenylboronic acid, FIG. 3, (or other glucose binding molecules with a non-covalent bond such as lectins in FIG. 4), which form covalent crosslinks within the diols on the polyols in the hydrogel (FIG. 5). The volume of this hydrogel changes with free glucose concentration due to a competitive binding effect to phenylboronic acid with a covalent bond or other GBM with a noncovalent bond.

When the glucose concentration increases near the implant area, additional amounts of free glucose diffuse into the hydrogel and displace polyols from the binding sites of the immobilized phenylboronic acid (FIG. 3). This reduces the hydrogel crosslink density, and thus the hydrogel swells. This type of GSF eliminates problems with pH-sensitive hydrogels such as oxygen deficit and enzyme degradation that have hindered the development of implantable electrochemical glucose sensors using pH-sensitive hydrogels.

Optimization of GSF for Glucose-dependent Elongation

The optimization of GSF for glucose-dependent elongation depends upon these factors: the target range of glucose concentrations, the required degree of accuracy, hydrogel composition, and the size of the filament. Except for hydrogel composition and degree of accuracy, most of these factors are easily estimated beforehand. The glucose-sensitive hydrogel is preferably designed to measure blood glucose concentration with a degree of accuracy of 20 mg/dL or better. The length of the hydrogel filament is preferably less than 1 cm, and the target glucose concentration range of the sensor is preferably between 50 mg/dL to 450 mg/dL with a less than 20 mg/dL increment. Response time is preferably within a few minutes. The hydrogel slab may be a single piece of hydrogel or made up of a plurality of pieces of hydrogel. A micro fiber of hydrogel or a bundle of micro fibers can be used in order to provide a faster response time.

Synthesis of a GSF Based on GOX Immobilization

Synthesis conditions for pH-sensitive hydrogels have been well established. Based on these previous studies, we preferably use acrylamide (AM) or dimethylacrylamide (DmAM) as a polymer backbone, sodium acrylate (NaAA) as the pH-sensitive pendant group, and N,N'-methylene-bis-acrylamide (MBA) as the crosslinker. To obtain the acidic hydrogel copolymers with different properties, the ratios of the monomers and MBA cross-linker are preferably varied as shown in TABLE 1.

TABLE 1

Relative amounts of reactants in each hydrogel

| Component | Mole ratios (%) of reactants (Sodium acetate buffer pH 5, 25° C.) | | | | |
|---|---|---|---|---|---|
| | Reaction 1 | Reaction 2 | Reaction 3 | Reaction 4 | Reaction 5 |
| AM | 70 | 50 | 30 | 70 | 70 |
| NaAA | 30 | 50 | 70 | 30 | 30 |
| MBA | 2.0 | 2.0 | 2.0 | 1.5 | 1.0 |
| APS | 0.001 | 0.001 | 0.001 | 0.001 | 0.001 |
| TEMED | 0.003 | 0.003 | 0.003 | 0.003 | 0.003 |

Each reaction preferably takes place by free radical solution polymerization in a 20 ml flask at ambient temperature. A total 5 g of monomers and cross-linker are preferably dissolved in 10 ml of sodium acetate (pH 5.0) buffer to dissolve pendant groups in a 20 ml flask. The polymerization mixture is thoroughly mixed for 10 min, and is then bubbled with argon gas to remove oxygen for 20 min in an ice bath. Polymerization and cross-linking is preferably achieved by adding an initiator ammonium persulfate (APS), preferably in an amount of about 1%. The mixture solution is poured between two glass plates and kept at 4° C. until polymerization is completed. The glass plates are separated with spacers in order to obtain gels of desired thickness. After completion of the reaction, the gel is washed 3 times with PBS buffer ([I]=0.15) and stored at 4° C. in PBS buffer until use. The above procedure provides a pH sensitive hydrogel that is not sensitive to any particular analyte, and which may be useful in the invention as a reference hydrogel.

To make the hydrogel glucose sensitive, GOX enzymes and catalase are added. The enzymes GOX and catalase are introduced during the reaction stages which result in physical immobilization of the enzymes within the hydrogel. The amount of GOX varies between 20 and 200 mg per 10 ml of polymerization mixture; the GOX (Sigma products) contains a fixed weight fraction of catalase. Additional catalase is added as a quencher of hydrogen peroxide in order to decrease peroxide-mediated GOX deactivation, which would limit the useful life of the hydrogel.

In our studies thus far, thin pH-sensitive hydrogels show faster kinetic volume change than thick hydrogels. The hydrogels also show good reversibility for cyclic changes in salt, pH, and glucose concentrations.

Synthesis of a Series of GSF Based on a Competitive Binding Mechanism with Covalent Bond To produce a competitive binding hydrogel, glucose-conjugated and GBM (Glucose Binding Molecule)-conjugated vinyl monomers are synthesized. These conjugated monomers are then co-polymerized with crosslinkers and either cationic or anionic monomers. The crosslinker introduces a small number of permanent crosslinks into the hydrogel in order to keep hydrogel integrity at all free glucose concentrations.

This novel type of GSF contains immobilized GBM and polyols such as poly(vinyl alcohol) (PVA), with other pendant groups as necessary to achieve the desired sensitivity, response, and durability. The GBM is preferably a phenylboronic acid having a high binding affinity and binding specificity for saccharides such as glucose. The volume of this hydrogel responds to the environmental concentration of free glucose via a competitive binding mechanism that is very specific and does not require oxygen or enzymes. When immobilized GBM reversibly binds to diol groups of polyols, it creates crosslinks in the hydrogel that act to resist hydrogel swelling.

As shown in FIG. 3, when the concentration of glucose in the solution surrounding the hydrogel increases, free glucose diffuses into the gel and displaces diol moieties from the binding sites of the GBM, thereby decreasing the density of crosslinks in the hydrogel. Since hydrogel volume has an inverse dependence on crosslink density, the hydrogel swells. Thus, as with the GOX-based hydrogels, free glucose concentration variations can be detected by measuring filament length changes in the GSF. FIG. 3 shows an example of GSF elongation in the presence of free glucose due to competitive binding to the immobilized GBM between the free glucose and the covalently bound diols in PVA in the GSF.

Synthesis of Boronic Acid-containing Complex Gels

A boronic acid group in a tetrahedral anionic form makes covalent complexes with diol compounds including PVA and glucose. Due to this unique characteristic of a boronic acid group, it can be incorporated into a polymer backbone as a GBM. The hydroxyl groups of PVA in complexes with a boronic acid group of the polymer backbone can substitute with glucose hydroxyl groups. Such a competitive binding between glucose and hydroxyl groups of PVA against boronic acid moieties induces a change in the crosslinking density, thus, the complex hydrogels can swell or de-swell in response to the concentration of glucose. Basic tertiary amino groups in a polymer backbone contribute to the formation of the stable complexes of boronic acid and diol compounds (PVA and glucose) at the physiological pH in aqueous solutions. A boronic acid based hydrogel may be prepared with N-[3-(N,N'-dimethylamino)propyl] acrylamide (DMAPAA) and 3-methacrylamidophenyl-boronic acid (MAAPBA) as described previous investigators.

To prepare MAAPBA, 0.1 M of 3-aminophenylboronic acid hemisulfate is preferably dissolved in 100 ml of deionized water and stirred with a magnetic stirring bar. The pH of the solution is preferably adjusted to pH 4.8 by the addition of NaOH solution and cooled to 4° C. in an ice bath. After cooling, 0.1 M of 1-[3(dimethylamino)propyl]3-ethylcarbodiimide hydrochloride and 0.1 M of acrylic acid is preferably added to the solution and then the pH of the solution is preferably again adjusted to pH 4.8. After one hour of stirring, MAAPBA is preferably extracted with diethyl ether and after the removal of diethyl ether by evaporation, MAAPBA is preferably recrystallized from water.

To synthesize a boronic acid-containing copolymer, poly (DMAA-co-MAAPBA-co-DMAPAA-co-BMA) copolymer is preferably synthesized by radical copolymerization in ethanol. MAAPBA, N,N-dimethylacrylamide (DMAA), isobutylmethacrylate (BMA), DMAPAA, and ethanol is preferably put together into a 50 ml glass flask. The solution is preferably stirred with a magnetic stirring bar and bubbled with nitrogen gas for 20 min. Ammonium persulfate (APS) is preferably used as an initiator. After adding APS to the solution the copolymerization reaction is preferably carried out for 3 hours at 70° C. under nitrogen gas atmosphere with stirring. The product copolymer is preferably precipitated with diethyl ether and dried in vacuum.

To form a complexation of boronic acid-containing copolymer and PVA, 2 wt % boronic acid-containing copolymer dissolved in methanol and 2 wt % PVA solution in dimethyl sulfoxide (DMSO) is preferably mixed to form complexes between hydroxyl groups of PVA and boronic acid group. The complex polymer solution then inject between glass plates with the gap set using a Teflon spacer (0.2 mm). After drying at 45° C. for 20 h, the complex gel slab is preferably separated from the two glass plates with a razor blade and cut into a 0.5 mm by 10 mm filament using a cutter.

Synthesis of a Series of GSF Based on a Competitive Binding Mechanism With Non-covalent Bond This new type of GSF contains immobilized glucose binding molecules (GBM) and immobilized glucose moieties, with other pendant groups as necessary to achieve the desired sensitivity, response, and durability. The GBM are preferably be a lectin like Con A, glucokinase, xylose isomerase, and isolactin I. The volume of this hydrogel responds to the environmental concentration of free glucose via a competitive binding mechanism that is very specific and does not require oxygen or enzymes. When immobilized GBM reversibly binds to immobilized glucose moieties, it creates crosslinks in the hydrogel that act to resist hydrogel swelling. As shown in FIG. 4, when the concentration of glucose in the solution surrounding the hydrogel increases, free glucose diffuses into the gel and displaces immobilized glucose moieties from the binding sites of the GBM, thereby decreasing the density of crosslinks in the hydrogel. Since hydrogel volume has an inverse dependence on crosslink density, the hydrogel swells. Thus, as with the GOX-based hydrogels, free glucose concentration variations can be detected by measuring filament length changes in the chip.

The competition hydrogel contains both GBM and hexose saccharides chemically or physically immobilized on the hydrogel backbone. FIG. 4 shows an example of GSF elongation in the presence of free glucose due to competitive binding to the immobilized GBM between the free glucose and the chemically bound glucose in the hydrogel.

Immobilization of Glucose and Con A to Polymer Backbone

Several glucose-conjugated and GBM-conjugated vinyl monomers are preferably synthesized as described below. These conjugated monomers are then co-polymerized with crosslinkers and either cationic or anionic monomers. The crosslinker introduces a small number of permanent crosslinks into the hydrogel in order to keep hydrogel integrity at all free glucose concentrations.

For binding of a conjugated hexose to Con A with high affinity, a minimal configurational structure with unmodified hydroxyl groups on the C-3, C-4, and C-6 position is essential. The binding affinity of a hexose saccharide to Con A is dependent upon the configurational factor at C-2 hydroxyl group, since mannose with the axial position at C-2 hydroxyl group has 40 times higher binding affinity for Con A than mannose with the equatorial position at C-2 hydroxyl group. As an example, a vinyl group is preferably attached at the C-1 position, forming allyl glucose (AG) through an etherification reaction of glucose with allyl alcohol (FIG. 5).

Figure 6:
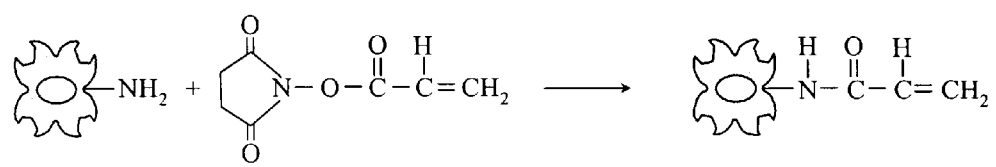
FIG. 6 is a schematic diagram for the conjugation of a vinyl group to Con A with N-acryloxysuccinimide.

Con A is preferably chemically and physically immobilized into the hydrogel network following a procedure described in previous studies. Vinyl groups are preferably conjugated to Con A as shown in FIG. 6. The conjugated Con A is preferably purified using dialysis or ultrafiltration with a membrane (molecular weight cutoff of 10,000 KDa). The concentrations of conjugated vinyl groups on Con A are preferably determined by spectrophotometry, and the purified Con A concentrated using a speed vacuum drier. Con A is preferably chemically incorporated into the hydrogel network via the vinyl groups.

N-(2,2)-dimethylaminoethyl methacrlate (DMA), HPMA, acrylamide (AM), sodium acrylate (NaAA), MBA, ammonium persulfate (APS), N,N,N',N'-tetramethylethylenediamine, and the vinyl conjugates are preferably used to synthesize the GSF. The amount of conjugated Con A and conjugated glucose are preferably varied between 0.1 mM to 10 mM to find a GSF with optimal response to glucose concentrations of 50 mg/dL (0.03 mM) to 1000 mg/dL (6.3 mM). The backbone of the polymer is preferably composed of neutral monomers such as AM and HPMA and/or charged monomers such as NaAA and DMA. Density of the charged pendant groups is preferably varied to adjust the swelling ratio of the GSF.

The reaction ratio of AG to Con A, monomer, and cross-linking agents is preferably optimized to achieve the greatest response of hydrogel filament length to change in glucose concentration. Alternatively, p-nitrophenyl-α-D-mannopyranoside, p-nitrophenyl-α-D-glucopyranoside, glucosyloxyethyl methacrylate (GEMA), N-glucosylacrylamide (NGAM), and disaccharide-based monomers containing a glucose moiety preferably used instead of glucose for immobilization on the polymer. Also, other GBM such as glucokinase, xylose isomerase, and isolactin I are preferably immobilized on the polymer chemically or physically instead of Con A.

Glucose Binding Molecules and Other Analyte Binding Molecules

TABLE 2 contains a list of glucose and glucose binding partners to which the method and biosensor of the invention can be applied. The glucose binding partner molecule should bind the glucose with sufficiently high specificity. For examples, an antibody (ABM) tightly binds with an antigen (glucose) with a high specificity.

TABLE 2

| Analyte Binding Molecule (ABM) | Glucose |
|---|---|
| Antibody | Antigen |
| Enzyme and Kinase | Cofactor, Substrate, and Inhibitor |
| Protein A | IGG |
| Concanavalin A | D-Sugar |
| Lectins | Carbohyrates |
| Boronic acid | 1,2-cis-Diol sugars |
| Thiol | Cystein |
| Receptors (Cell membrane receptors, Cytosol receptors, and Nuclear receptors) | Growth factors, Hormones, Metal ions, Modifed molecules such as phospholated. |
| Heparin, DNA, and RNA | Protamine, Polylysine, Polyarginine |
| Poly U, Poly A, Poly Lysine, and Poly Arginine | Nucleic acid |
| Triazine dye | Nucleotide |
| Commassie blue and Azure A | Arginine, Lysine, and Proteins |
| Metal binding molecules including chelating agents | Ca ion, Mg ion, etc |

Semipermeable Membrane

The semipermeable membranes used in the biosensor of the invention, such as membrane 14, FIG. 1, are preferably made of a material rigid enough to substantially constrain the GSF to one-dimensional expansion or contraction. The semipermeable membrane is permeable to the passage of glucose, oxygen, and gluconic acid. However, it is totally impermeable to the passage of blood clots, cells, and proteins.

The semipermeable membrane is preferably an inert, nontoxic material that maintains its integrity when implanted in humans. A suitable biocompatible semipermeable material, to minimize immune reactions and to prevent protein and cell absorption, is preferably selected from the following groups of polymers: cellulose acetate, methyl cellulose, polyvinyl alcohol, polypropylene, HEMA, tetraacrylated poly(ethylene glycol) (PEG), and/or polyurethane. Cross-linked aliphatic polyurethanes are preferably synthesize in order to enhance biocompatibility and to retard biodegradation due to its controllable permeability.

The porosity of the polyurethane membrane affects both immunoprotection and the selective permeation of molecules. Membrane thickness is also important for immunoprotection, as well as for diffusion of glucose and oxygen. The maximal pore volume fraction and the minimum possible thickness are important to achieve rapid diffusion of glucose and oxygen through the semipermeable membrane. Also, the pore volume fraction, the average pore diameter, and wall thickness affect the mechanical strength of the membrane. Different porosities and thickness (0.01 mm to 0.5 mm) are formed to find the optimal membrane. The pore size is preferably controlled between 0.1 micrometer to 15 micrometer by varying the crystal size of the salt particles dispersed in the polyurethane solution before crosslinking. Preferably, different sizes of salt particles such as sodium fluoride and zinc hydroxide are used at various concentrations. Different concentrations of linoleic acid, heparin and/or PEG are preferably incorporated in the polyurethane in order to increase the crosslinking efficiency and biocompatibility. The crosslinker dicumyl peroxide is preferably purified several times and used in the polyurethane network. The salt crystals imbedded in the polyurethane film is preferably leached out by submerging the film in water with sodium fluoride, acetic buffer, or in EDTA solution. This creates the porosity. Next the membrane is preferably dried for more than 2 days at room temperature. The polyurethane is preferably coated or bonded over the GSF.

Hydrogel Displacement Measurement Using pH-sensitive Hydrogel

Figure 7A:
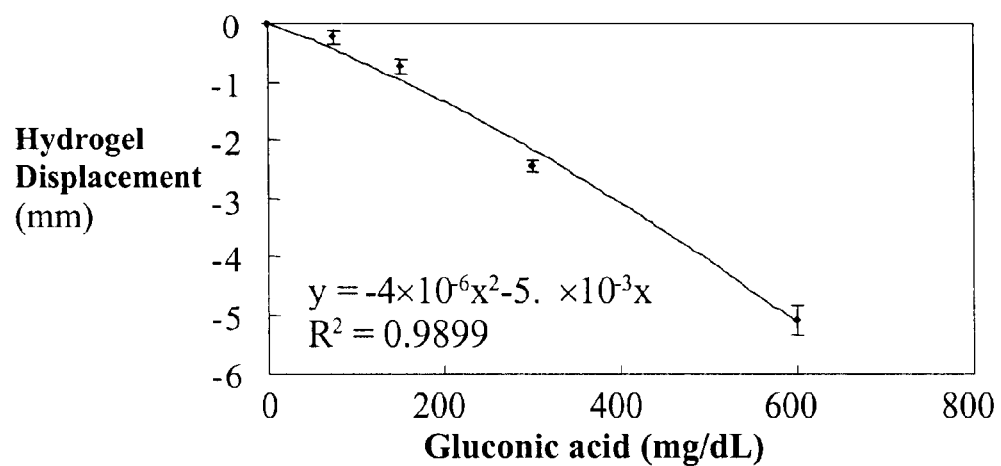
FIG. 7A depicts changes in hydrogel displacement length for an acidic pH-sensitive hydrogel.
Figure 7B:
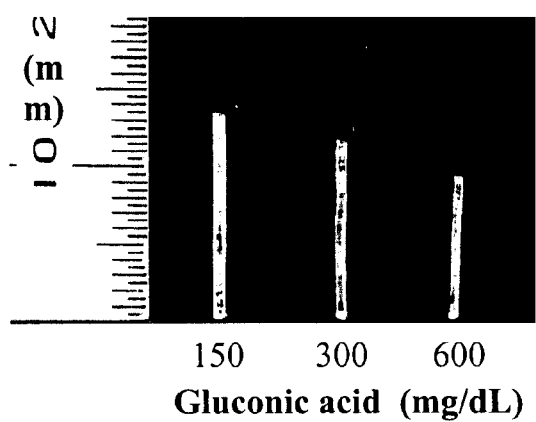
FIG. 7B depicts a scanned image of a hydrogel at different displacement lengths.

FIGS. 7A and 7B depict the measurement of displacement volume changes for a test system using a pH-sensitive hydrogel subjected to varying concentrations of gluconic acid. The hydrogel was composed of AM, MBA, and NAAA. Slices of hydrogel (0.5 mm width, 0.4 mm thickness and 13.97 mm length) were immersed in citric buffer (ionic strength, $[I]=0.15$) containing different gluconic acid concentrations (0, 75, 150, 300, and 600 mg/dL), after 30 minutes changes in hydrogel length were measured using a ruler (Mitutoyo calipers). A plot of the displacement vs. gluconic acid concentration is depicted in FIG. 7A, while FIG. 7B represents a computer-scanned picture of the hydrogel slice, showing the change in hydrogel length with gluconic acid concentration. FIG. 7A shows hydrogel displacement in millimeter for an acidic pH-sensitive hydrogel as a function of gluconic acid concentration. The hydrogel is composed of acrylamide/sodium acrylate/N, N'-methylene-bis-acrylamide (MBA), mole ratio 50:50:2. Hydrogel displacement is defined as hydrogel gel length at concentration X minus hydrogel length at a reference condition. Negative displacement represents hydrogel contraction; positive displacement represents hydrogel expansion. In the experiment of results shown in FIG. 7A, the hydrogel displacement increases with increasing gluconic acid concentration, which corresponds to a decrease in pH within the hydrogel. From 0 to 600 mg/dL, the displacement is 5.09 mm, which is a contraction of about 36% compared to the reference solution. FIG. 7B shows a hydrogel scan image produced with an EPSON perfection 636U scanner, for hydrogels in different gluconic acid concentrations.

The pH sensitivity of hydrogel displacement can also be controlled by varying the elements of the polymer composition, such as the pKa of ionizable pendant groups, the amount of ionizable pendant group, crosslinking density, crosslinker type, and hydrophobicity of the polymer backbone.

The glucose-dependent elongation of the GSF on the GSF can be predicted by measuring the swelling ratio of the unconfined GSF synthesized in solutions of varying concentration of free glucose. The elongation ratios are preferably proportional to the free glucose concentration. Slices of GSF are preferably immersed in a PBS buffer or serum with different amounts of glucose (50–450 mg/dL), and the changes in GSF length and mass are preferably monitored.

Hydrogel and Ultrasound Image Scanning Device

The ultrasound scanner 15, FIG. 1, is designed to measure the glucose concentration based on the length displacement of the glucose-sensitive filament in the biosensor chip 10 implanted under the subcutaneous layer of human skin. The glucose-sensitive hydrogel 11 is enough for the ultrasound image capture because the hydrogel is dense compared to membrane 14 and supporting block 13, and has a smooth surface with a regular shaped.

The hydrogel filament 11 in the biosensor chip 10 is stimulated by the change of glucose level in body fluid contacting membrane 14, and swells in length depending on the concentration level of glucose in the fluid. The ultrasound transducer 15 located outside of the body scans the biosensor chip 10 and captures the image of the hydrogel filament 11. An ultrasound image-processing unit estimates the displacement of the hydrogel filament, which is converted to the corresponding glucose concentration level based on a calibration table or a constant sensitivity value governing the relationship between the glucose level and the displacement.

In general, the ultrasound wave's depth of travel into the human body depends on the frequency of the wave. The sound wave of lower frequency penetrates deeper into the human body. Conversely, the lateral resolution, which determines the ability to resolve objects placed side-by-side, increases with increased frequency. In order to increase lateral resolution for the present invention, it is feasible to use a higher frequency ultrasound wave than ordinarily used. The implantation of the hydrogel under the subcutaneous layer in the present invention takes advantage of higher ultrasound image resolution. With the biosensor chip 10 implanted about 5 mm under the skin, the travel distance of ultrasound wave, from the outer skin to the implanted hydrogel, is expected to be less than 10 mm including epidermis and dermis layer, and the distance allows using the higher ultrasound frequency that penetrates shallow but gives a higher image resolution.

There are commercially available ultrasound devices with lateral resolutions of several micrometers, and current ultrasound manufacturers have the technological capability to develop the ultrasound device of higher resolution. In order to achieve high glucose concentration resolution in the glucose scanner, the ultrasound device should provide the highest lateral resolution possible. Furthermore, the glucose-sensitive hydrogel filament is developed in order to give the maximum change of swelling length within the proposed glucose concentration range. Those who are skilled in the ultrasound field can accommodate an ultrasound scanner to the specific needs of the swelling displacement measurement.

The ultrasound beam leaving the transducer travels two zones, a near zone and a far zone. In the near zone, the ultrasound beam is focused so that it gives better reflection resulting in better resolution. In the far zone, the beam begins to lose focus and as a result, scattered image information returns. Although the length of the near zone is determined by several factors such as probe dimension, lens, and frequency, it is preferable that the ultrasound device is designed to cover the implanted hydrogel within its near zone to provide the higher image resolution.

One concern which may come up with ultrasound scanning is acoustic shadowing, a negative effect to an object laid under another object after the overlaid object reflects most of the sound energy and leaves not enough energy for the next object. For the present invention, acoustic shadowing does not affect the hydrogel image because there is no significant object between the wave source and the hydrogel, except the semi-permeable membrane that can be fabricated with material of low density to permit a large amount of wave penetration.

The glucose-sensitive hydrogel can accommodate certain reporter moieties to improve its image quality when scanned by ultrasound. These moieties are Silicates, Aluminosilicates, Organosilaoxanes, carbosilanes, Silazanes, Ferrocene, Metallo porphyrin, Amine-transition metal complexes, Phthalocyanines, Silicone, Ge, Sn, and phosphazene.

Design of Glucose Sensitive Biosensor Chip

FIGS. 8A–8C show a biosensor chip similar to that shown in FIG. 1. When used to measure glucose levels, it can be referred to glucochip. The glucose-sensitive hydrogel filament 81 sits in a groove 82 in the glucochip, with the top side covered by the semi-permeable membrane 83. The groove 82 and the membrane 83 confine the hydrogel filament 81 so that it can only swell in the longitudinal direction. The hydrogel filament 81 will freely elongate or shrink along the longitudinal groove depending on the glucose concentration surrounding the glucochip. Initially the glucochip is filled with a buffer such as PBS. The outer shape of the support block 84 can be rectangular as shown in FIGS. 1 and 8A–8C, or may be cylindrical, cubical, or any other shape that allows easy implantation and affords comfort to users. The support block 84 and membrane 83 will protect the hydrogel against deformation so that the hydrogel is not distorted and elongates linearly along groove 82. Stainless steel, Teflon, ceramic, or a composite material can be used to fabricate the support block 84. The support block materials should have a reasonably different density or acoustic impedance from the hydrogel filament 81 in order to be distinguished from hydrogel image when captured as an ultrasound image.

The biocompatible semipermeable membrane 83 covers the hydrogel-filled groove 82 by being secured to support block 84 over groove 82. Glucose-containing body fluid is free to pass through the membrane and is able to stimulate the hydrogel. The membrane will have a thickness on the order of microns with a significantly lower density than the hydrogel filament 81, and will be transparent to the incoming ultrasound wave without absorbing the sound energy so that the hydrogel 81 beneath membrane 83 can be imaged without interference. In addition, the membrane 83 will be biocompatible and has sufficient stiffness to prevent the hydrogel filament 81 from swelling in directions perpendicular to the longitudinal axis.

Also, optionally but desirably, scale marks 85 may be provided on the glucochip support block 84 adjacent membrane 83 and groove 82 to be used to compensate for any discrepancy between the actual displacement of the implanted hydrogel and the displacement of the hydrogel image. The compensation factor can be obtained from the ratio of the actual distance between scale marks 85, which is known from fabrication of the glucochip, and the distance between scale marks on the ultrasound image. The scale marks 85 will be formed of a substance that can be sharply distinguished by the scanner such as a metal when the support block is not metal.

The size of the glucochip depends largely on the dimensions of the glucose-sensitive hydrogel filament. Accordingly, the length of filament depends on the intended glucose resolution, maximum hydrogel elongation, ultrasound image resolution, and intended glucose range. TABLE 3 shows one example of the specific values reflecting the relationship among filament length, image resolution, hydrogel elongation, glucose resolution, and glucose range. Another consideration that determines the filament size is response time to changes in analyte concentration; generally, more rapid response times are preferred.

Three factors affecting response time are the length of the hydrogel filament 81; the length-to-width ratio; and diffusion time of analyte into the hydrogel. Shorter hydrogel filaments exhibit shorter response times, as do filaments with greater ratios of length Y to both width X and depth Z. Diffusion time is related to the depth Z: the smaller the Z, the more rapid the diffusion and/or equilibration of analyte from the test fluid in the hydrogel. Also, the greater the surface area (X multiplied by Y) that is open to contact with the test fluid, the more rapid diffusion will be, but to promote a maximal elongation response it is necessary to limit X somewhat. Based on the factors to the filament dimensions, in a presently preferred embodiment, the hydrogel slab is shaped as a filament having a lengthwise dimension Y, which is substantially greater than width and depth dimensions X and Z. In a preferred embodiment, the lengthwise dimension Y is between about 0.2 cm and about 2 cm, more preferably between about 0.2 cm and about 1 cm, and Y is between about 5 and about 50 times each of X and Z. For example, when Y is 1 cm and each of X and Z is $\frac{1}{10}$ times of Y, the width and depth are 0.1 cm.

Once the dimension of the hydrogel filament including length Y, width X, and depth D is determined by considering the factors such as glucose resolution and response time, the dimension of glucochip can be drawn from the size of the hydrogel filament. The length L of the channel 82 in FIG. 8B will be larger than the maximum swelling length of the hydrogel filament, and the width W and the depth D of the channel 82 in FIGS. 8A and 8C will be the same as the width X and depth Z of the hydrogel filament. Since the chip is to be implanted, it is desirable that the chip itself is as small as possible as long as it can accommodate the size of the hydrogel filament determined from the factors, and preferably less than 2.5 cm in length and no more than 1.2 cm in width and depth.

Figure 9A:
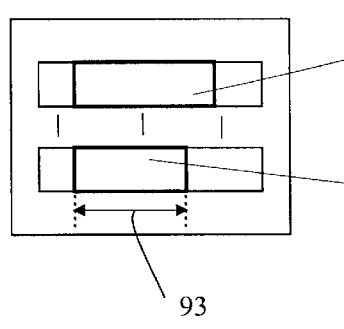
FIG. 9A depicts a biosensor chip having both analyte-sensitive and reference hydrogels in case of no compensation.
Figure 9B:
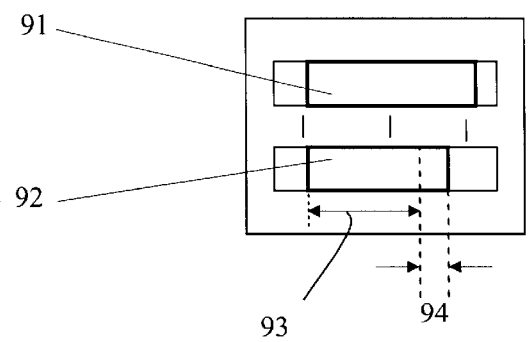
FIG. 9B depicts a biosensor chip having both analyte-sensitive and reference hydrogels in case of compensation.

FIGS. 9A and 9B show a glucochip that includes both a glucose sensitive hydrogel filament 91 and a reference hydrogel filament 92. The glucose-sensitive hydrogel 91 is designed to respond only to glucose. However, in the case that the glucose-sensitive hydrogel reacts to some substance other than glucose, examining the reference hydrogel filament 92 that is also placed on the glucochip can compensate for the non-specific swelling. This hydrogel is chemically identical to the glucose-sensitive hydrogel, with the exception that it has no GOX or GBM on the hydrogel backbone, so it does not respond to glucose. The original length of the reference hydrogel 93 is known from the fabrication of the glucochip. When the reference hydrogel swells or contracts from its original length, the deviation 94, if any, will be either added to or subtracted from the swelling displacement of the glucose-sensitive hydrogel. In FIG. 9A, the swelling displacement of the glucose-sensitive hydrogel does not need to be compensated because the reference hydrogel remains at its original length. On the other hand, FIG. 9B demonstrates a swelling displacement of the glucose-sensitive hydrogel 91 that needs to be compensated by the deviation 94 in length of the reference hydrogel 92.

Figure 10A:
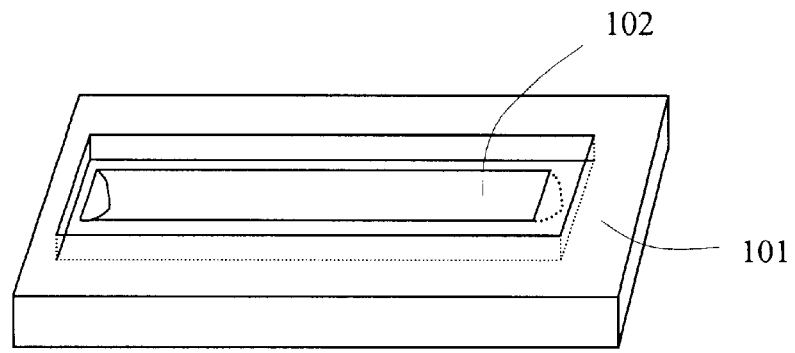
FIG. 10A depicts an alternate embodiment of the biosensor support block.
Figure 10B:
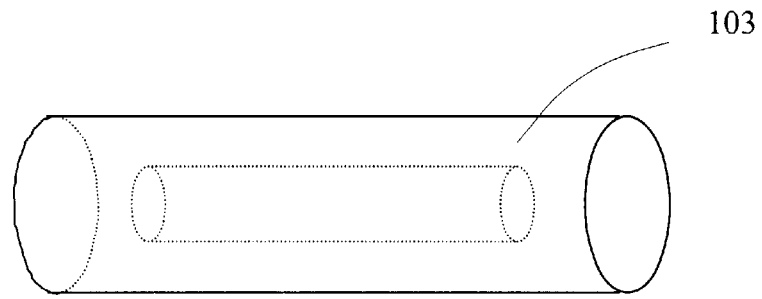
FIG. 10B depicts another alternate embodiment of the biosensor support block.
Figure 10C:
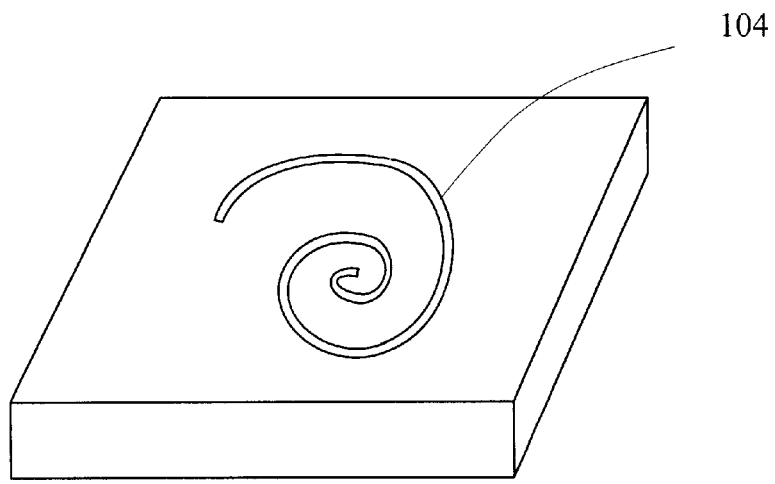
FIG. 10C depicts still another embodiment of the biosensor support block.

While the embodiment of FIGS. 8A, 8B, and 8C is based on an elongated rectangular hydrogel filament 81 in a rectangular receiving groove 82, in an alternate configuration depicted in FIG. 10A the hydrogel is in the form of an elongated split cylinder in a semi-cylindrical receiving groove 102. In this embodiment, groove 102 in the block 101 is covered with a semipermeable membrane in a manner similar to that in FIG. 8A. In still another embodiment, FIG. 10B, a cylindrical hydrogel filament is encased in a cylindrical or tubular support block 103 made of rigid material which is either semi-permeable or has openings covered with semi-permeable material to permit diffusion from the surrounding environment (a patient's body fluids, or a test solution) into the hydrogel. Still another configuration is arranged in a coil or spiral configuration, FIG. 10C. Groove 104 may have a rectangular or semicircular cross section. The coil or spiral design allows a much longer filament of hydrogel to be used, which can provide enhanced volume displacement response, yet keeps the overall size of the chip acceptably small for long-term implantation.

Ultrasound Image Scanning System

Figure 11:
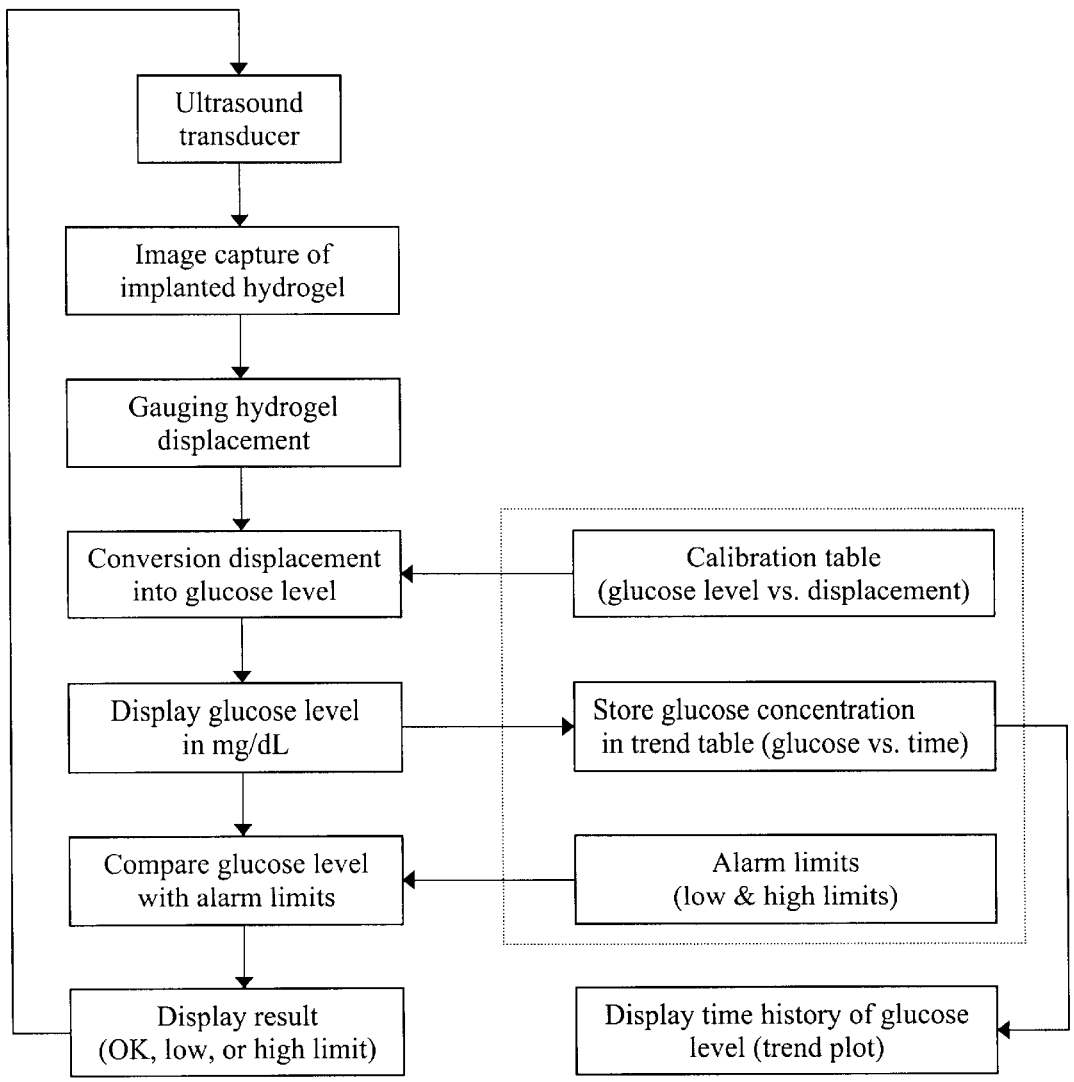
FIG. 11 is a flow chart of a glucose scanning system.

FIG. 11 shows the flow chart of the glucose monitoring procedure using the hydrogel image. The ultrasound transducer scans the implanted glucochip in order to provide an image of the hydrogel filament on the chip. The captured image is processed to determine the filament swelling displacement. Glucose level is estimated by converting the displacement using the calibration table or the constant sensitivity value that present the relationship between swelling displacement and glucose level. This calibration table or the sensitivity value is determined empirically from measurements in vitro. The glucose level is displayed to users through a readout device, and it can be stored in memory in the form of a database as long as the memory space is available. The stored glucose levels can be plotted with respect to time in order to provide the time-variant glucose level change for a long-term. The glucose scanner alerts users immediately when the glucose level is out of a pre-determined range stored in memory.

Figure 12:
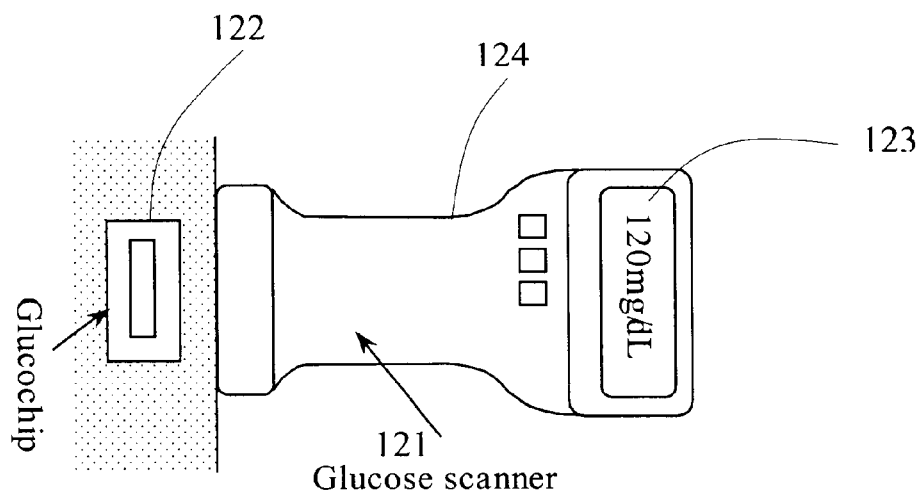
FIG. 12 depicts an example of a portable glucose scanner.

For the glucose scanning system, the ultrasound image capturing function and the post processing function such as gauging, converting, and monitoring are incorporated into one structure, both in hardware and software. A personal computer can be used as the means for managing the large amount of database and data backup in connection with the ultrasound glucose scanning system. The physical dimensions of the glucose scanner can be miniaturized so that users are comfortable carrying and using it. It is expected that the weight can be less than 1 Kg and the size about that of a personal wireless phone. FIG. 12 shows a possible design for a portable glucose scanner 121 with built in ultrasound transducer 122, display 123, and control buttons 124.

The resolution of glucose measurements depends on initial hydrogel length, hydrogel elongation, image resolution, and intended glucose range. TABLE 3 shows an example of the specific factors and values in order to realize a glucose resolution of 20 mg/dL in the glucose scanning system. The glucose scanner should provide enough image resolution to measure the minimum change of glucose concentration, in the order of 20 mg/dL. The scanner needs to detect a hydrogel filament length displacement change of 100 $\mu$m, which is estimated as follows. Assuming an initial filament length of about 8 mm, which changes by 25% over the glucose concentration range of interest (50–450 mg/dL). Then, in order to detect a change in glucose concentration of 20 mg/dL, the ultrasound scanner must detect a filament length change of 8 mm×0.25×20 (mg/dL)/(450–50 mg/dL)= 100 $\mu$m. It is also feasible that the glucose resolution can be 10 mg/dL by either increasing hydrogel elongation to 50%, increasing ultrasound image resolution to 50 $\mu$m, or increasing initial hydrogel length to 16 mm.

TABLE 3

An example of determination factors for glucose resolution

| Glucose-sensitive hydrogel | Initial length | 8 mm |
| --- | --- | --- |
| | Elongation | 25% |
| | Elongation length | 2 mm |
| Glucochip | Length | 15 mm |
| Ultrasound | Image resolution | 100 μm |
| Glucose Measurement | Range | 50–450 mg/dL |
| | Span | 400 mg/dL |
| | Resolution | 20 mg/dL |

Figure 13:
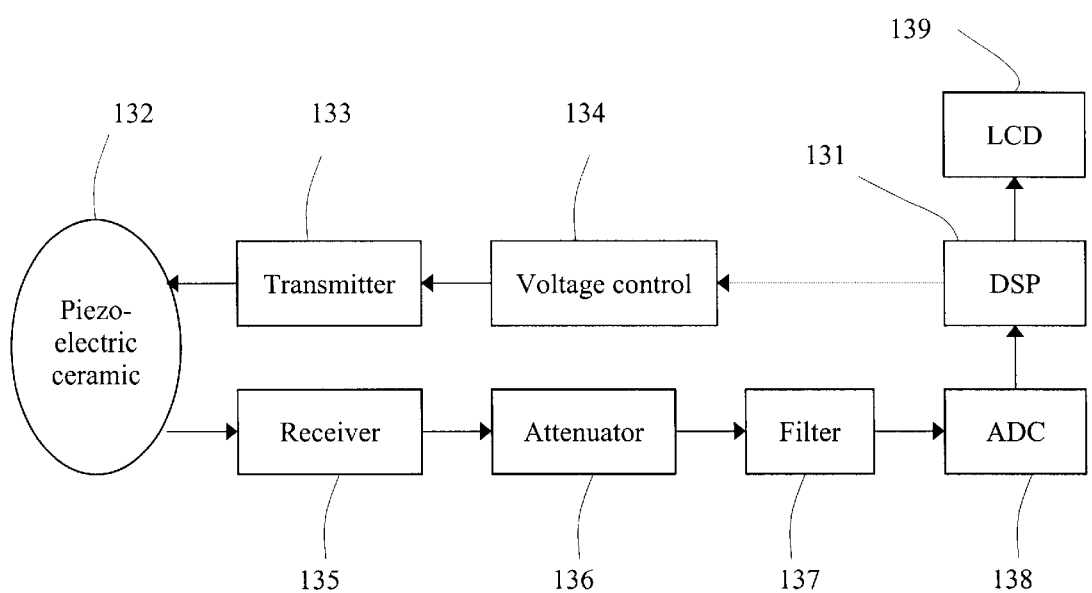
FIG. 13 is a block diagram of an ultrasound glucose scanning system.

As one embodiment of the invention, the architecture of the glucose scanning system can be developed around a microprocessor core that is the TMS320C6000 DSP (Digital Signal Processing) microprocessor from Texas Instruments, which offers a high processing speed to the benefit of the ultrasound image processing. In addition, TMS320C6000 DSP is designed for low power operation, which is advantageous for long-term operation of a battery-operated portable scanning device. FIG. 13 shows a simplified electrical block diagram for a portable glucose scanning system. The voltage controller 134 controls the excitation voltage of the transmitter 133 to the piezoelectric ceramic crystal 132 that emits the ultrasound wave. The ultrasound wave is reflected from the hydrogel filament inside the glucochip and returned to the same piezoelectric ceramic 132, which generates an electric voltage signal in the receiver 135 depending on the returned wave. Since the dynamic range of the returned signal is large, the attenuator 136 is necessary to keep the voltage signal within the input range of a high speed A/D converter 138, and the filter 137 rejects frequencies due to noise outside the wave bandwidth. The filtered signal enters to the A/ID converter 138, and the DSP 131 processes the digitally converted voltage data from the A/D converter in order to provide the filament swelling displacement from the hydrogel image. The DSP manages the conversion of the swelling displacement to a glucose concentration value, and displays that value in the LCD 139. The DSP also performs other supplementary functions such as data storage and alarm monitoring. The programming of the DSP is well within the skill of a programmer familiar with the particular microprocessor used for DSP.

Biosensor Chip with Multi Hydrogel Filaments

Figure 14:
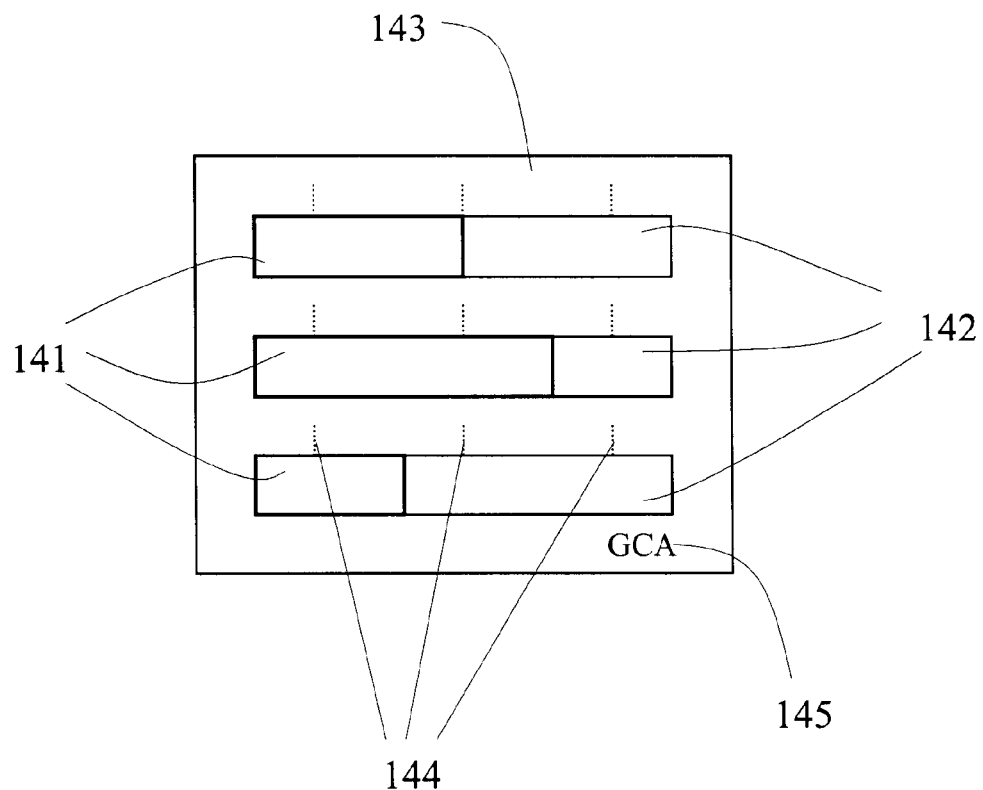
FIG. 14 depicts another embodiment of biosensor chip design showing multiple hydrogel filaments.

It is possible to measure not only glucose level with a biosensor chip of the invention, but also any analyte level in addition to or other than glucose level with a single biosensor chip, having a plurality of specific analyte-sensitive hydrogel filaments. FIG. 14 shows one embodiment of the biosensor chip. Each hydrogel filament 141 is placed into a closed groove 142 that gives a pathway for swelling displacement of each hydrogel filament. The substance-sensitive hydrogel filaments 141 swell proportionally depending on the level of substance inside of body. The swelling displacement represents the concentration level of a substance.

In FIG. 14, the biosensor chip has analytes-sensitive hydrogel filaments 141, grooves 142, scale marks 144, a chip identifier 145, and a biocompatible support block 143. Hydrogel filaments can be synthesized to be exclusively sensitive to specific analytes such as glucose, cholesterol, antibiotics, pH, NaCl, and so on. Any number and combination of analyte sensitive hydrogels can be incorporated into a simple support block in order to measure analyte concentration levels of concern. The use of a reference hydrogel as described for FIGS. 9A and 9B can similarly be used for the compensation due to non-specific response of each hydrogel in the biosensor chip of FIG. 14. The chip identifier 145 printed on the container provides information about the hydrogels used in the chip. For example, the letters GCA, indicated at 145, printed on the biosensor chip, means that the chip has glucose-sensitive, cholesterol-sensitive, and pH-sensitive hydrogels. The support block 143 enclosing the hydrogels is biocompatible and semi-permeable. This allows body fluids to pass through to contact and respond to the concentration level of concern. The scale marks 144 are used as a reference scale in order to find the actual swelling displacement when the biosensor chip is captured as an image.

Alternative Image Scanning System

An object of the invention is to measure from outside a body the swelling displacement of a hydrogel implanted in the body. Image capture to allow determination of the displacement from the image can be acquired by any satisfactory system that will image the hydrogel that is inside the body from outside the body. Systems such as CT(Computerized Tomography Imaging) and MRI (Magnetic Resonance Imaging), as well as the described ultrasound imaging system are satisfactory. Those who are skilled in the fields concerned can create the image scanning systems necessary for the scanning the implanted biosensor.

CT is based on x-ray technology with an array of x-ray detectors instead of conventional film so that a computerized system can process the returned x-ray in order to obtain the multiple of images of different body layers. The proposed implantable biosensor can use CT as alternative inside-of-body image scanning device.

Based on the NMR(Nuclear Magnetic Resonance) technology, MRI is a medical means for providing high quality images of the inside of the human body with a high resolution of less than 10 micron. The hydrogel filament of the biosensor of the invention can be imaged by an MRI system.

The glucose-sensitive hydrogel can accommodate certain reporter moieties to improve its image quality when scanned by MRI and CT. The following TABLE 4 shows candidates for such moieties.

TABLE 4

| Imaging Modality | Reporter Moiety |
| --- | --- |
| MRI | Paramagnetic substances, such a Gd and Mn, and iron oxide |
| CT image | Heavy elements, such as I, Br, and Ba |

Figure 15:
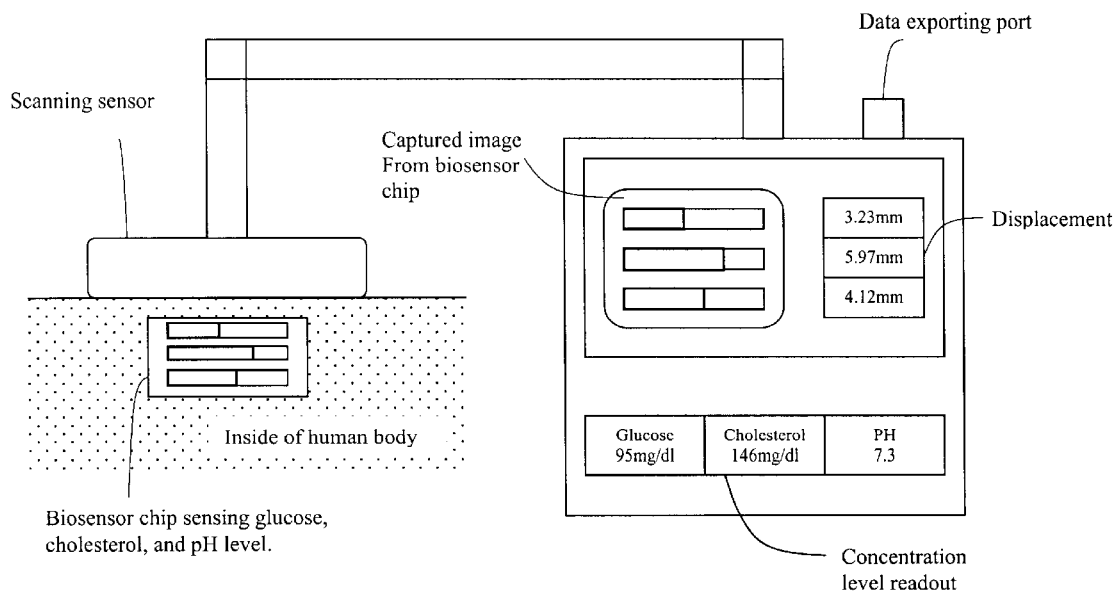
FIG. 15 depicts an image scanning system for non-continuous diagnostic purpose.

FIG. 15 shows one example of the image-scanning system for non-continuous diagnostic purposes. A biosensor chip capable of sensing glucose, cholesterol, and pH levels as described in connection with FIG. 14 is implanted for measuring the respective concentration levels. The image scanning system captures the image of the biosensor chip and processes the images to acquire the swelling displacement. Individual concentration levels are obtained from each swelling displacement by using a sensitivity value or table representing the relationship between concentration level and displacement. The readout monitor displays the captured image, the displacement, and each concentration level. Those who have a biosensor chip implanted inside the body can easily obtain concentration levels simply by using an image scanning sensor. A health provider can make this image-scanning sensor available. In addition, the scanned data can be sent to third parties through data transmission means such as the Internet, wireless communication, telephone, etc.

Figure 16:
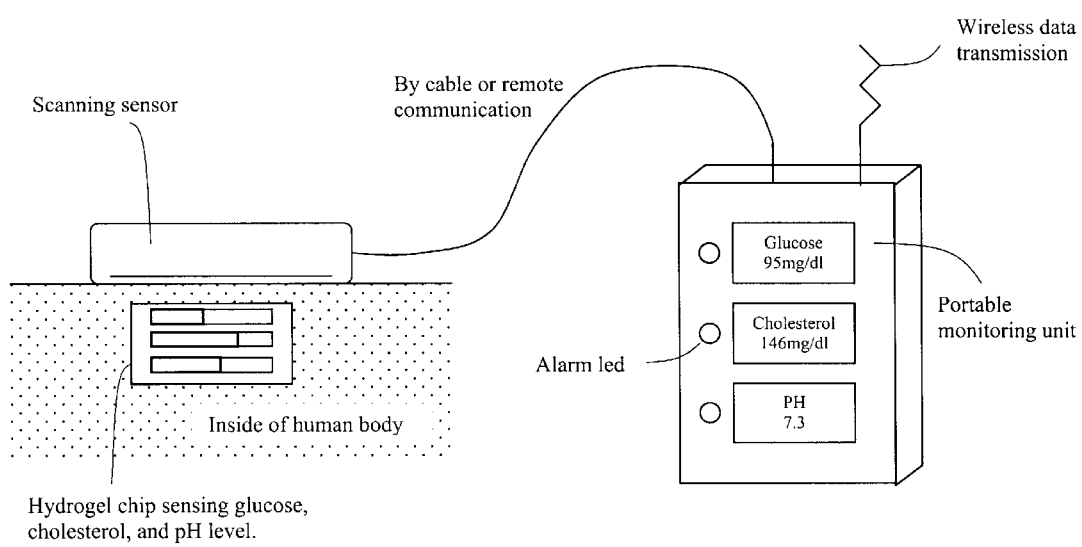
FIG. 16 depicts an image scanning sensor attached to a human body with a portable continuous glucose monitor.
Figure 17:
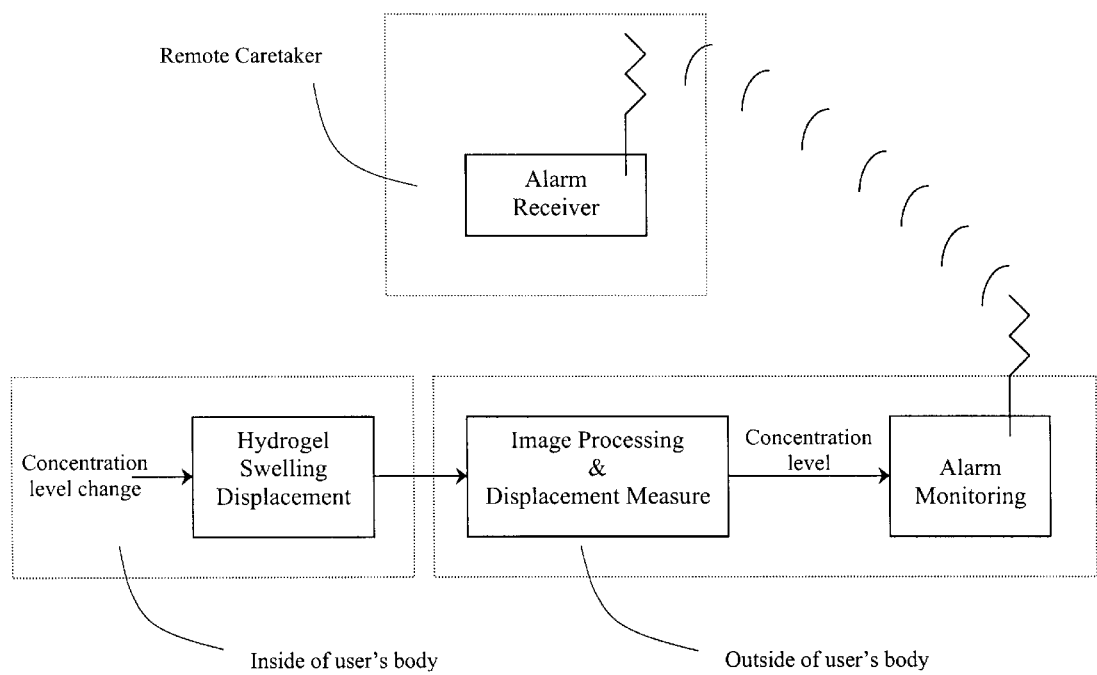
FIG. 17 is a block diagram for a monitor with an automatic alarm system.

FIG. 16 shows that the image scanning devices can be portable and attached to the body where the biosensor chip is implanted. This allows for continuous monitoring of the analytes of concnern. Moreover, the device can include an alarm system in order to inform any emergency condition to the user and/or remote caretakers via wireless data transmission facilities (FIG. 17).

It is also feasible that the glucose level or other analytes level can be measured not only from one dimensional displacement changes of a hydrogel filament, but also from two or three dimensional swelling changes of a hydrogel. The image scanning systems used, such as ultrasound imaging scanner, can accommodate the 2 or 3 dimensional measurement of hydrogel dimension change and can quantify the amount of the area or volume change due to the hydrogel swelling for the analyte measurement based on the calibration data between glucose level and 2 or 3 dimensional change of the hydrogel filament.

Whereas the invention has been described with regard to particular embodiments thereof currently contemplated as the best mode of carrying out the invention in actual practice, it should be realized that various changes may be made in adapting the invention to various other embodiments without departing from the broader inventive concepts set forth herein and in the claims that follow.

What is claimed is:

1. A biosensor system comprising:
   an implantable analyte-sensitive hydrogel slab chemically configured to vary its displacement volume according to changes in concentration of an analyte in a body fluid in a body in which the hydrogel slab is implanted; and
   scanning means configured to quantifiably detect changes in the displacement volume of the hydrogel slab when it is implanted within the body by capturing an image of at least a portion of the hydrogel slab.

2. A biosensor system comprising:
   an implantable analyte-sensitive hydrogel slab chemically configured to vary its displacement volume according to changes in concentration of an analyte in a body fluid in a body in which the hydrogel slab is implanted;
   wherein the hydrogel slab is disposed in a support block formed of a rigid or semi-rigid support material, the support block having one or more openings permitting the body fluid to contact the hydrogel; and
   scanning means configured to quantifiably detect changes in the displacement volume of the hydrogel slab when it is implanted within the body.

3. The biosensor system of claim 2, wherein the opening(s) are covered by a semipermeable membrane which is configured to permit passage of the analyte and prevent passage of proteins into the openings.

4. The biosensor system of claim 2, wherein the support block is sized and configured to permit expansion of the hydrogel slab substantially in only one dimension.

5. The biosensor system of claim 2, wherein the support block is characterized by dimensions x, y, and z, and the support block is sized and configured to limit expansion of the hydrogel in dimensions x and z, and to permit expansion of the hydrogel in the y direction.

6. The biosensor system of claim 2, wherein the support block includes a groove in which the hydrogel slab is disposed, and a semi-permeable membrane covers the hydrogel slab and the groove, the membrane being configured to permit passage of the analyte and prevent passage of proteins into the groove.

7. The biosensor system of claim 2, wherein the support block has three dimensions, at least one of said dimensions sized to prevent expansion of the hydrogel slab, and at least one of said dimensions sized to accommodate the hydrogel at its maximal displacement volume.

8. The biosensor system of claim 7, wherein two of said dimensions are sized to prevent expansion of the hydrogel slab.

9. The biosensor system of claim 2, wherein the support block has scale means located adjacent the hydrogel slab for providing known scale dimensional values to compare with the hydrogel slab.

10. The biosensor system of claim 2, wherein the support block includes a groove in which the hydrogel slab is disposed, and further includes a second groove in which a reference hydrogel slab is disposed, the reference hydrogel being chemically configured to lack analyte sensitivity.

11. The biosensor system of claim 2, wherein the hydrogel slab has pendant charged groups selected to confer pH-sensitivity, such that the hydrogel swells or shrinks according to changes in pH.

12. The biosensor system of claim 11, wherein the pendant charged groups confer a net negative charge on the hydrogel slab.

13. The biosensor system of claim 11, wherein the pendant charged groups confer a net positive charge on the hydrogel slab.

14. The biosensor system of claim 2, wherein the hydrogel slab is composed by polymerizing one or more chemical subunits selected from the group consisting of: acrylamide, dimethyl-acrylamide, sodium acrylate, hydroxypropyl methacrylate, 2-hydroxyethyl methacrylate, diethylaminoethyl methacrylate, isobutyl methacrylate, butyl methacrylate, isopropyl methacrylate, n-alkyl methacrylate, acrylamide, N-isopropylacrylamide, N-tert-butylacrylamide, N,N-dimethylamide, N,N'-methylene-bis-acrylamide, polyvinyl alcohol, N-[3-(N,N'-dimethylamino)propyl]-acrylamide, styrene, N,N'-methylene-bis-acrylamide, polyvinyl alcohol, and 3-methacrylimidophenylboronic acid.

15. The biosensor system of claim 2, wherein the hydrogel slab is chemically configured to vary its displacement volume according to the concentration of glucose in a human body fluid.

16. The biosensor system of claim 15, wherein the hydrogel further includes a quantity of immobilized molecules having glucose oxidase activity.

17. The biosensor system of claim 16, wherein the glucose-binding moieties are selected from the group consisting of: boronic acids, phenylboronic acid, inactivated glucose-binding enzymes, glucose binding sites derived from glucose-binding enzymes, glucose-specific antibodies, lectins, and glucose binding sites derived from lectins.

18. The biosensor system of claim 16, wherein the complementary molecules are selected from the group consisting of: diols, poly(vinyl) alcohol, and hexose saccharides.

19. The biosensor system of claim 15, wherein the hydrogel has
   a quantity of glucose-binding moieties immobilized therein, and
   a quantity of complementary molecules immobilized therein, said complementary molecules configured to selectively bind to said glucose-binding moieties.

20. The biosensor system of claim 2, wherein the support material is selected from the group consisting of: Teflon, rigid or semi-rigid plastics, stainless steel, ceramics, and composite materials.

21. A biosensor system comprising:
   an implantable analyte-sensitive hydrogel slab shaped as a filament having a lengthwise dimension Y which is substantially greater than first and second width dimensions X and Z, and chemically configured to vary its displacement volume according to changes in concentration of an analyte in a body fluid in a body in which the hydrogel slab is implanted;

a support block formed of a support material, said hydrogel filament being disposed within the support block; and scanning means configured to quantifiably detect changes in the displacement volume of the hydrogel slab when it is implanted within the body.

22. The biosensor system of claim 21, wherein the support block is sized and configured to permit expansion of the hydrogel filament in only the Y dimension.

23. The biosensor system of claim 22 wherein the lengthwise dimension Y is between about 0.2 cm and about 2 cm.

24. The biosensor system of claim 22 wherein the lengthwise dimension of the filament is between about 0.2 cm and 1 cm.

25. The biosensor system of claim 21, wherein the lengthwise dimension of the filament is between about 5 and about 50 times each of the first and second widths.

26. The biosensor system of claim 21, wherein X and Z are each between about 0.1 cm and about 1 cm.

27. A biosensor system comprising:

an implantable analyte-sensitive hydrogel slab chemically configured to vary its displacement volume according to changes in concentration of an analyte in a body fluid in a body in which the hydrogel slab is implanted; and ultrasound detection means configured to quantifiably detect changes in the displacement volume of the hydrogel slab when it is implanted within the body.

28. The biosensor system of claim 27, further including computing means operably associated with the scanning means for translating a measured value of the displacement volume to a corresponding analyte concentration, and producing an output signal reflective thereof.

29. The biosensor system of claim 28, further including a continuous-monitoring alarm unit operably disposed to receive an output signal reflective of the displacement volume or of the analyte concentration corresponding to the displacement volume, said alarm system configured to compare the output signal to a pre-determined safe range and to provide a warning to the patient and/or to caretakers when the output signal falls outside the safe range.

30. The biosensor system of claim 7, wherein the scanning unit further includes wireless transmission means operably connected and configured to transmit an output signal reflective of the displacement volume or of the analyte concentration corresponding to the displacement volume to a remote monitoring device.

31. The biosensor system of claim 27, wherein the ultrasound detection means forms part of a scanning unit, the scanning unit being portable and sized and shaped to be handheld.

32. The biosensor system of claim 27, wherein the ultrasound detection means forms part of a scanning unit configured for attachment on the surface of a patient's body adjacent to the location at which the sensor chip is implanted.

33. A biosensor system comprising:

an implantable analyte-sensitive hydrogel slab chemically configured to vary its displacement volume according to changes in concentration of an analyte in a body fluid in a body in which the hydrogel slab is implanted; and means for magnetic resonance scanning capable of detecting changes in the displacement volume of the hydrogel slab when it is implanted within the body.

34. A biosensor system comprising:

an implantable analyte-sensitive hydrogel slab chemically configured to vary its displacement volume according to changes in concentration of an analyte in a body fluid in a body in which the hydrogel slab is implanted; and means for computerized tomography capable of detecting changes in the displacement volume of the hydrogel slab when it is implanted within the body.

35. An implantable biosensor chip for implantation into a patient's body comprising:

a support block formed of rigid or semi-rigid, biocompatible material, a groove in the support block having one or more openings permitting penetration of a patient's body fluid, a semipermeable membrane configured to permit passage of the analyte and prevent passage of proteins into the groove; and an analyte sensitive hydrogel slab disposed within the groove, said hydrogel slab being chemically configured to vary its displacement volume according to changes in concentration of an analyte in the body fluid, said hydrogel slab being further configured to be detectable by externally-based means for imaging body structures, said hydrogel slab being shaped as a filament having a length dimension Y which is substantially greater than first and second width dimensions X and Z, and wherein the groove is sized to permit expansion of the hydrogel slab in the length dimension and to substantially prevent expansion of the hydrogel slab in one or both of the width dimensions.

36. The biosensor chip of claim 35 wherein the lengthwise dimension Y is between about 0.2 cm and about 2 cm.

37. The biosensor chip of claim 36, wherein the lengthwise dimension of the filament is between about 5 and about 50 times each of the first and second widths.

38. The biosensor chip of claim 35, wherein the support block further has a second groove containing a reference hydrogel slab, the second groove having one or more openings permitting the body fluid to contact the reference hydrogel slab, and the reference hydrogel slab being insensitive to analyte concentration but otherwise substantially identical in dimensions and chemical composition to the analyte-sensitive hydrogel.

39. The biosensor chip of claim 35, wherein the support block is formed of a material selected from the group consisting of: Teflon, rigid or semi-rigid plastics, stainless steel, ceramics, and composite materials.

40. The biosensor chip of claim 35, wherein the hydrogel slab has pendant charged groups selected to confer pH-sensitivity, such that the hydrogel swells or shrinks according to changes in pH.

41. The biosensor chip of claim 40, wherein the pendant charged groups are selected from the group consisting of: 3-[N,N-dimethylamino)propyl]acrylamide, -(2,2-diethylaminoethyl) methacrylate, N(2,2-dimethylaminoethyl) methacrylate, N-(2,2-dimethylaminoethyl) acrylamide, N,N-dimethyl acrylamide, vinyl pyridine, acrylic acid, methacryl acid, sodium acryl acid, and 2-acrylamino-2-methyl propanesulfonic acid.

42. The biosensor chip of claim 40, wherein the pendant charged groups confer either a net negative charge or a net positive charge on the hydrogel slab.

43. The biosensor chip of claim 35, wherein the hydrogel slab is composed of one or more chemical subunits selected from the group consisting of: acrylamide, dimethylacrylamide, sodium acrylate, hydroxypropyl methacrylate, 2-hydroxyethyl methacrylate, diethylaminoethyl methacrylate, isobutyl methacrylate, butyl methacrylate, isopropyl methacrylate, n-alkyl methacrylate, acrylamide, N-isopropylacrylamide, N-tert-butylacrylamide, N,N-dimethylacrylamide, N,N'-methylene-bis-acrylamide, polyvinyl alcohol, N-[3-(N,N'-dimethylamino)propyl] acrylamide, styrene, and 3-methacryl-amidophenylboronic acid.

44. The biosensor chip of claim 35, wherein the hydrogel slab is chemically configured to vary its displacement volume according to the concentration of glucose in a human body fluid.

45. The biosensor chip of claim 44, wherein the hydrogel further includes a quantity of immobilized molecules having glucose oxidase activity.

46. An implantable biosensor chip for implantation into a patient's body comprising:
    a support block formed of rigid or semi-rigid, biocompatible material;
    a groove in the support block having one or more openings permitting penetration of a patient's body fluid;
    a semipermeable membrane configured to permit passage of the analyte and prevent passage of proteins into the groove;
    an analyte sensitive hydrogel slab disposed within the groove, said hydrogel slab being chemically configured to vary its displacement volume according to changes in concentration of an analyte in the body fluid, and said hydrogel slab being further configured to be detectable by externally-based means for imaging body structures; and
    scale means disposed on said support block and located adjacent the hydrogel slab for providing known scale dimensional values to compare with the hydrogel slab, said scale means being detectable in simultaneity with the hydrogel slab.

47. An implantable biosensor chip for implantation into a patient's body comprising:
    a support block formed of rigid or semi-rigid, biocompatible material,
    a groove in the support block having one or more openings permitting penetration of a patient's body fluid,
    a semipermeable membrane configured to permit passage of the analyte and prevent passage of proteins into the groove;
    an analyte sensitive hydrogel slab disposed within the groove, said hydrogel slab being chemically configured to vary its displacement volume according to changes in concentration of glucose in a human body fluid, and said hydrogel slab being further configured to be detectable by externally-based means for imaging body structures;
    a quantity of glucose-binding moieties immobilized in the hydrogel; and
    a quantity of complementary molecules immobilized in the hydrogel, said complementary molecules configured to selectively bind to said glucose-binding moieties.

48. The biosensor chip of claim 47, wherein the glucose-binding moieties are selected from the group consisting of: boronic acids, phenylboronic acid, 3-methylacrylamido-phenylboronic acid, 3-acrylamidophenylboronic acid, inactivated glucose-binding enzymes, glucose binding sites derived from glucose-binding enzymes, glucose-specific antibodies, lectins, concanavalin A, and glucose binding sites derived from lectins.

49. The biosensor chip of claim 47, wherein the complementary molecules are selected from the group consisting of: diols, poly(vinyl)alcohol, glucosyloxyethylmethacrylate, acryl glucose, N-(2-D-glucose)acrylamide, and hexose saccharides.

50. The biosensor chip of claim 47, wherein the groove has three dimensions x, y, and z, and wherein the groove is sized to permit expansion of the hydrogel slab in the y-dimension only.

51. An implantable biosensor chip for implantation into a patient's body comprising:
    a support block formed of rigid or semi-rigid, biocompatible material,
    a groove in the support block having one or more openings permitting penetration of a patient's body fluid, said groove having three dimensions x, y, and z, and wherein the groove is sized to permit expansion of the hydrogel slab in the y-dimension only;
    a semipermeable membrane configured to permit passage of the analyte and prevent passage of proteins into the groove; and
    an analyte sensitive hydrogel slab disposed within the groove, said hydrogel slab being chemically configured to vary its displacement volume according to changes in concentration of an analyte in the body fluid, said hydrogel slab being further configured to be detectable by externally-based means for imaging body structures, and wherein under an initial condition the hydrogel slab has a width $x_0$, thickness $z_0$, and length $y_0$, $y_0$ being between about 5 and about 50 times greater than both $x_0$ and $y_0$.

52. The biosensor chip of claim 51, wherein $y_0$ is between about 0.2 cm and about 2 cm.

53. The biosensor chip of claim 52, wherein the hydrogel slab is made up of a plurality of individual pieces of hydrogel.

54. A method of monitoring an analyte in a patient's body fluid in situ, comprising the steps of:
    implanting a biosensor chip having a support block formed of rigid or semi-rigid, biocompatible material; a groove in the support block having one or more openings permitting penetration of a patient's body fluid: a semipermeable membrane configured to permit passage of the analyte and prevent passage of proteins into the groove; and an analyte sensitive hydrogel slab disposed within the groove, said hydrogel slab being chemically configured to vary its displacement volume according to changes in concentration of an analyte in the body fluid, and said hydrogel slab being further configured to be detectable by externally-based means for imaging body structures in the patient's body;
    providing means for scanning the hydrogel slab in the biosensor chip implanted within the patient's body, and
    arranging and operating the hydrogel scanning means to detect changes in the displacement volume of the hydrogel.

55. The method of claim 54, wherein the step of providing hydrogel scanning means is a step of providing ultrasound detection means disposed and configured to detect changes in the displacement volume of the hydrogel.

56. The method of claim 54, wherein the step of providing hydrogel scanning means is a step of providing means for magnetic resonance scanning.

57. The method of claim 54, where including a step of providing computing means operably associated with the scanning means for translating a measured value of the displacement volume to a corresponding analyte concentration, and producing an output signal reflective thereof.

58. The method of claim 57, further including a step of calibrating the displacement volume against the concentration of analyte in a solution, said calibration step including steps of:

contacting the sensor chip with a series of solutions having different known concentrations of analyte, storing a value of the displacement volume for each of the solutions, and constructing a calibration curve for translating a measured displacement volume to a corresponding analyte concentration.

59. The method of claim 58, wherein the analyte is glucose.

60. A biosensor system comprising:

an implantable sensor chip including an analyte-sensitive hydrogel slab chemically configured to vary its displacement volume according to changes in concentration of an analyte in a patient's body fluid; and image scanning means configured to image the hydrogel slab and to quantify changes in the displacement volume.

61. The biosensor system of claim 60, wherein the sensor chip further includes a support block made of a rigid or semi-rigid support material, and the hydrogel slab is disposed within a groove formed in the block, the groove having one or more openings permitting the body fluid to contact the hydrogel slab.

62. The biosensor system of claim 61, wherein the groove is sized and configured to permit only one-dimensional elongation or contraction of the hydrogel slab.

63. The biosensor system of claim 61, wherein the sensor chip further includes a reference hydrogel slab disposed within a second groove, there reference hydrogel being chemically configured to be insensitive to analyte concentration but otherwise substantially identical to the analyte-sensitive hydrogel, and the second groove also having an opening permitting contact between the body fluid and the reference hydrogel slab.

64. The biosensor system of claim 61, wherein the sensor chip further includes scale marks disposed adjacent to the hydrogel slab, said scale marks being detectable by the scanning means in simultaneity with the hydrogel slab.

65. The biosensor system of claim 60, wherein the hydrogel slab is chemically configured to vary its displacement volume according to the concentration of glucose in a human body fluid.

66. The biosensor system of claim 65, wherein the hydrogel further includes a quantity of immobilized molecules having glucose oxidase activity.

67. The biosensor system of claim 66, wherein the glucose-binding moieties are selected from the group consisting of: boronic acids, phenylboronic acid, inactivated glucose-binding enzymes, glucose binding sites derived from glucose-binding enzymes, glucose-specific antibodies, lectins, and glucose binding sites derives from lectins.

68. The biosensor system of claim 65, wherein the hydrogel has a quantity of glucose-binding moieties immobilized therein, and a quantity of complementary molecules immobilized therein, said complementary molecules configured to selectively bind to said glucose-binding moieties.

* * * * *

UNITED STATES PATENT AND TRADEMARK OFFICE
CERTIFICATE OF CORRECTION

PATENT NO.    : 6,751,491 B2
DATED         : August 16, 2004
INVENTOR(S)   : Seok Lew et al.

It is certified that error appears in the above-identified patent and that said Letters Patent is hereby corrected as shown below:

<u>Title page,</u>
Item [73], Assignee, should show:
-- Assignee: M-Biotech, Inc., Salt Lake City, UT --

Signed and Sealed this

Ninth Day of November, 2004

JON W. DUDAS
*Director of the United States Patent and Trademark Office*